US006492399B1

(12) United States Patent
Dull et al.

(10) Patent No.: US 6,492,399 B1
(45) Date of Patent: Dec. 10, 2002

(54) PHARMACEUTICAL COMPOSITIONS AND METHODS FOR USE

(75) Inventors: Gary Maurice Dull, Lewisville; Craig Harrison Miller, Winston-Salem; William Scott Caldwell, Winston-Salem; Srishailkumar Basawannappa Hadimani, Winston-Salem, all of NC (US)

(73) Assignee: Targacept, Inc., Winston-Salem, NC (US)

( * ) Notice: Subject to any disclaimer, the term of this patent is extended or adjusted under 35 U.S.C. 154(b) by 0 days.

(21) Appl. No.: 09/327,774

(22) Filed: Jun. 7, 1999

Related U.S. Application Data

(63) Continuation-in-part of application No. 09/098,133, filed on Jun. 16, 1998, now Pat. No. 6,232,316.

(51) Int. Cl.$^7$ .......................... A61K 31/44; A61K 31/04; A61K 31/035

(52) U.S. Cl. .......................... 514/345; 514/740; 514/744

(58) Field of Search ................................. 514/351, 345, 514/357, 358, 740, 744; 546/300

(56) References Cited

U.S. PATENT DOCUMENTS

| | | | | |
|---|---|---|---|---|
| 4,551,460 A | | 11/1985 | Tilley .......................... | 514/267 |
| 4,672,066 A | | 6/1987 | Carson et al. ............... | 514/256 |
| 4,786,646 A | | 11/1988 | Guthrie et al. ............... | 514/346 |
| 4,857,335 A | | 5/1989 | Bohm .......................... | 424/455 |
| 4,863,933 A | | 9/1989 | Cooper et al. ............... | 514/314 |
| 4,880,829 A | | 11/1989 | Hansen, Jr. et al. ......... | 514/445 |
| 5,114,969 A | | 5/1992 | Chung et al. ................. | 514/514 |
| 5,597,919 A | | 1/1997 | Dull et al. .................... | 544/242 |
| 5,616,716 A | * | 4/1997 | Dull et al. .................... | 546/300 |
| 5,629,325 A | | 5/1997 | Lin et al. ...................... | 514/318 |
| 5,663,356 A | | 9/1997 | Ruecroft et al. ............. | 546/300 |
| 5,811,442 A | | 9/1998 | Bencherif et al. ........... | 514/384 |
| 5,861,423 A | * | 1/1999 | Caldwell et al. ............. | 514/351 |
| 5,914,337 A | | 6/1999 | Martin et al. ................. | 514/357 |

FOREIGN PATENT DOCUMENTS

| | | | | |
|---|---|---|---|---|
| DE | 24 05 930 A1 | 2/1974 | | |
| EP | 0 094 080 A2 | 11/1983 | .......... | C07D/471/04 |
| EP | 0 142 057 A2 | 5/1985 | .......... | C07D/233/04 |
| EP | 0 199 845 B1 | 11/1986 | .......... | C07C/103/30 |
| EP | 0 222 099 A2 | 5/1987 | .......... | C07C/103/30 |
| EP | 0 299 379 A1 | 7/1987 | .......... | C07D/103/30 |
| EP | 0 302 389 B1 | 2/1989 | .......... | C07D/213/36 |
| EP | 0 405 391 A1 | 1/1991 | .......... | C07D/213/55 |
| EP | 0 559 495 A1 | 3/1993 | .......... | A61K/31/465 |
| EP | 0 559 413 A1 | 11/1993 | .......... | A61K/31/465 |
| EP | 0 571 139 A1 | 7/1996 | .......... | A61K/31/44 |
| FR | 2031868 | 11/1970 | ............ | A01N/9/00 |
| JP | 52 134094 | 11/1977 | | |
| JP | 54 006639 | 3/1979 | | |
| WO | WO 96/20599 | 7/1996 | .......... | A01N/43/40 |
| WO | WO96/20600 | 7/1996 | .......... | A01N/43/40 |
| WO | WO96/20929 | 7/1996 | .......... | C07D/213/02 |
| WO | WO96/31475 | 10/1996 | .......... | C07D/213/38 |
| WO | WO96/36637 | 11/1996 | .......... | C07D/471/08 |
| WO | WO 97/40011 | 10/1997 | .......... | C07D/213/38 |
| WO | WO98/37071 | 8/1998 | .......... | C07D/213/64 |
| WO | WO98/45268 | 10/1998 | .......... | C07D/213/82 |
| WO | WO 99/07369 | 2/1999 | .......... | A61K/31/44 |
| WO | WO 00/07600 | 2/2000 | .......... | A61K/31/645 |

OTHER PUBLICATIONS

Hogberg et al., "Homallylic Amines Related to Zimeldine. A Comparative Study on Neuronal Serotonin and Norepinephrine Reuptake Based on Conformational Analysis," *J. Med. Chem.* 31:5 913–919 (1988).

International Search Report; Nov. 26, 1999; R.J. Reynolds Tobacco Company et al.; PCT/US99/12340; file ref:627–311. WO.

Caplus AN 1974:535967, RN 54127–22–9.

Caplus AN 1985:560530, RN 6021–23–4.

Caplus AN 1987:84609 RN 6021–23–4.

Caplus AN 1989:2314447, RN 319690–13–2.

Caplus AN 1991:408582, RN 134162–95–1.

Caplus AN 1992:197012, RN 140681–92–1.

Caplus AN 1998: 618370, RN 1129–68–6.

Cashman, et al., "Stereoselective N–Oxygenation of Zimeldine and Homozimeldine by the Flavin–containing Monooxygenase,", *Drug Metab. Dispos.*, 16(4): 616–622 (1988) (Abstract).

Gold'faarb, et al., "Strength of Some Nicotine Series Base, "*Izv. Acad. Nauk SSR. Ser. Khim.*, (8):1883–1885 (1970) (Abstract).

Guthrie, et al, "Pentadienyl Carboxamide Derivatives as Antagonists of Platelet Activating Factor,", *J. Med. Chem.*, 32(8): 1820–1835 (1989) (Guthrie).

Hansch, et al., "A Survey of Hammett Substituent Constants and Resonance and Field Parameters", *Chem. Rev.*, 91:165–195 (1991).

(List continued on next page.)

*Primary Examiner*—Russell Travers
*Assistant Examiner*—Shengjun Wang
(74) *Attorney, Agent, or Firm*—Womble Carlyle Sandridge & Rice, PLLC

(57) ABSTRACT

Pharmaceutical compositions incorporate aryl substituted olefinic amine compounds. Representative compounds are (3E)-N-methyl-4-[3-(5-nitro-6-aminopyridin)yl]-3-buten-1-amine, (3E)-N-methyl-4-[3-(5-(N-benzylcarboxamido)pyridin)yl]-3-buten-1-amine, (4E)-N-methyl-5-[5-(2-aminopyrimidin)yl]-4-penten-2-amine, (4E)-N-methyl-5-(3-(5-aminopyridin)yl)-4-penten-2-amine, (3E)-N-methyl-4-(3-(5-isobutoxypyridin)yl)-3-buten-1-amine, (3E)-N-methyl-4-(3-(1-oxopyridin)yl)-3-buten-1-amine, (3E)-N-methyl-4-(3-(5-ethylthiopyridin)yl)-3-buten-1-amine, (4E)-N-methyl-5-(3-(5-trifluoromethylpyridin)yl)-4-penten-2-amine and (4E)-N-methyl-5-(3-(5-hydroxypyridin)yl)-4-penten-2-amine.

15 Claims, No Drawings

OTHER PUBLICATIONS

Högberg, et al., "Homoallylic Amines Related to Zimeldine, Comparative Study on Neuronal Serotonin and Norepinephrine Reuptake Based on Conformational Analysis,"*J. Med. Chem.*, 31(5):913–919 (1988).

International Search Report, PCT/US00/15560, Nov. 7, 2000.

Lippiello, et al., "RJR–2403: A Nicotinic Agonist with CNS Selectivity. II. In Vivo Characterization,"*J. Pharmacol. Exp. Ther.*, 279(3): 1422–1429 (1996).

Stoyanovich, et al, "Action of Potassium Amide on 5–Bromo–2(or 6)–Amino–3–(4–Methylaminobutyl)pyridine,", *Azv. Akad. Nauk SSSR.,. Ser. Khim.*, 11:2585–2590 (1970) (Abstract).

Tilley, et al., "Pyrido[2,1–b]quinazolinecarboxamide Derivatives as Platelet Activating Factor Antagonists,", *J. Med. Chem.*, 31(2):466–472 (1988) (Abstract).

Uspatfull AN 89:92535, RN 112102–59–7.

Uspatfull 89:67281, RN 126427–28–9.

Uspatfull AN 89:74192, RN 112860–50–1/

Yamamoto et al., "Nicotinoids as an Insecticide. VII. Cholinesterase Inhibition by Nicotinoids and Pyridylakylamines, Its Significance to Mode of Action,"*Agr. Biol. Chem.*, (*Tokyo*), 32(11): 1341–1348.

* cited by examiner

# PHARMACEUTICAL COMPOSITIONS AND METHODS FOR USE

CROSS-REFERENCE TO RELATED APPLICATION

The present application is a continuation-in-part of U.S. patent application Ser. No. 09/098,133, filed Jun. 16, 1998, now U.S. Pat. No. 6,232,316, the disclosure of which is incorporated herein by reference in its entirety.

BACKGROUND OF THE INVENTION

The present invention relates to pharmaceutical compositions, and particularly pharmaceutical compositions incorporating compounds that are capable of affecting nicotinic cholinergic receptors. More particularly, the present invention relates to compounds capable of activating nicotinic cholinergic receptors, for example, as agonists of specific nicotinic receptor subtypes. The present invention also relates to methods for treating a wide variety of conditions and disorders, and particularly conditions and disorders associated with dysfunction of the central and autonomic nervous systems.

Nicotine has been proposed to have a number of pharmacological effects. See, for example, Pullan et al. *N. Engl. J. Med.* 330:811–815 (1994). Certain of those effects may be related to effects upon neurotransmitter release. See for example, Sjak-shie et al., *Brain Res.* 624:295 (1993), where neuroprotective effects of nicotine are proposed. Release of acetylcholine and dopamine by neurons upon administration of nicotine has been reported by Rowell et al., *J. Neurochem.* 43:1593 (1984); Rapier et al., *J. Neurochem.* 50:1123 (1988); Sandor et al., *Brain Res.* 567:313 (1991) and Vizi, *Br. J. Pharmacol.* 47:765 (1973). Release of norepinephrine by neurons upon administration of nicotine has been reported by Hall et al., *Biochem. Pharmacol.* 21:1829 (1972). Release of serotonin by neurons upon administration of nicotine has been reported by Hery et al., *Arch. Int. Pharmacodyn. Ther.* 296:91 (1977). Release of glutamate by neurons upon administration of nicotine has been reported by Toth et al., *Neurochem Res.* 17:265 (1992). In addition, nicotine reportedly potentiates the pharmacological behavior of certain pharmaceutical compositions used for the treatment of certain disorders. See, Sanberg et al., *Pharmacol. Biochem. & Behavior* 46:303 (1993); Harsing et al., *J. Neurochem.* 59:48 (1993) and Hughes, *Proceedings from Intl. Symp. Nic.* S40 (1994). Furthermore, various other beneficial pharmacological effects of nicotine have been proposed. See, Decina et al., *Biol. Psychiatry* 28:502 (1990); Wagner et al., *Pharmacopsychiatry* 21:301 (1988); Pomerleau et al., *Addictive Behaviors* 9:265 (1984); Onaivi et al., *Life Sci.* 54(3):193 (1994); Tripathi et al., *JPET* 221: 91–96 (1982) and Hamon, *Trends in Pharmacol. Res.* 15:36.

Various nicotinic compounds have been reported as being useful for treating a wide variety of conditions and disorders. See, for example, Williams et al. *DN&P* 7(4):205–227 (1994), Arneric et al., *CNS Drug Rev.* 1(1): 1–26 (1995), Americ et al., *Exp. Opin. Invest. Drugs* 5(1):79–100 (1996), Bencherif et al., *JPET* 279:1413 (1996), Lippiello et al., *JPET* 279:1422 (1996), Damaj et al., *Neuroscience* (1997), Holladay et al., *J. Med. Chem* 40(28): 4169–4194 (1997), Bannon et al., *Science* 279: 77–80 (1998), PCT WO 94/08992, PCT WO 96/31475, and U.S. Pat. No. 5,583,140 to Bencherif et al., U.S. Pat. No. 5,597,919 to Dull et al., U.S. Pat. No. 5,604,231 to Smith et al., U.S. Pat. No. 5,616,716 to Dull et al. and U.S. Pat. No. 5,852,041 to Cosford et al. Nicotinic compounds are reported as being particularly useful for treating a wide variety of Central Nervous System (CNS) disorders.

CNS disorders are a type of neurological disorder. CNS disorders can be drug induced; can be attributed to genetic predisposition, infection or trauma; or can be of unknown etiology. CNS disorders comprise neuropsychiatric disorders, neurological diseases and mental illnesses; and include neurodegenerative diseases, behavioral disorders, cognitive disorders and cognitive affective disorders. There are several CNS disorders whose clinical manifestations have been attributed to CNS dysfunction (i.e., disorders resulting from inappropriate levels of neurotransmitter release, inappropriate properties of neurotransmitter receptors, and/or inappropriate interaction between neurotransmitters and neurotransmitter receptors). Several CNS disorders can be attributed to a cholinergic deficiency, a dopaminergic deficiency, an adrenergic deficiency and/or a serotonergic deficiency. CNS disorders of relatively common occurrence include presenile dementia (early onset Alzheimer's disease), senile dementia (dementia of the Alzheimer's type), Parkinsonism including Parkinson's disease, Huntington's chorea, tardive dyskinesia, hyperkinesia, mania, attention deficit disorder, anxiety, dyslexia, schizophrenia and Tourette's syndrome.

It would be desirable to provide a useful method for the prevention and treatment of a condition or disorder by administering a nicotinic compound to a patient susceptible to or suffering from such a condition or disorder. It would be highly beneficial to provide individuals suffering from certain disorders (e.g., CNS diseases) with interruption of the symptoms of those disorders by the administration of a pharmaceutical composition containing an active ingredient having nicotinic pharmacology and which has a beneficial effect (e.g., upon the functioning of the CNS), but which does not provide any significant associated side effects. It would be highly desirable to provide a pharmaceutical composition incorporating a compound which interacts with nicotinic receptors, such as those which have the potential to affect the functioning of the CNS, but which compound when employed in an amount sufficient to affect the functioning of the CNS, does not significantly affect those receptor subtypes which have the potential to induce undesirable side effects (e.g., appreciable activity at skeletal muscle and ganglia sites).

SUMMARY OF THE INVENTION

The present invention relates to aryl substituted amine compounds, and most preferably to aryl substituted olefinic amine compounds. Representative preferred compounds of the present invention include (3E)-N-methyl-4-[3-(5-nitro-6-aminopyridin)yl]-3-buten-1-amine, (3E)-N-methyl-4-[3-(5-(N-benzylcarboxamido)pyridin)yl]-3-buten-1-amine, (4E)-N-methyl-5-[5-(2-aminopyrimidin)yl]-4-penten-2-amine, (4E)-N-methyl-5-(3-(5-aminopyridin)yl)-4-penten-2-amine, (2S)-(4E)-N-methyl-5-[3-(5-isopropoxy-1-oxopyridin)yl)]-4-penten-2-amine, (3E)-N-methyl-4-(3-(5-isobutoxypyridin)yl)-3-buten-1-amine, (3E)-N-methyl-4-(3-(1-oxopyridin)yl)-3-buten-1-amine, (4E)-N-methyl-5-(3-(1-oxopyridin)yl)-4-penten-2-amine, (3E)-N-methyl-4-(3-(5-ethylthiopyridin)yl)-3-buten-1-amine, (4E)-N-methyl-5-(3-(5-trifluoromethylpyridin)yl)-4-penten-2-amine, (4E)-N-methyl-5-(3-(5-((carboxymethyl)oxy)pyridin)yl)-4-penten-2-amine, (4E)-5-(3-(5-isopropoxypyridin)yl)-4-penten-2-amine, and (4E)-N-methyl-5-(3-(5-hydroxypyridin)yl)-4-penten-2-amine.

The present invention also relates to methods for synthesizing certain aryl substituted amine compounds, such as the compounds of the present invention. Of particular interest are isolated enamiomeric compounds (i.e., compounds in a substantially pure form, as opposed to racemic mixtures), and methods for synthesizing such enaniomeric compounds in substantially pure form. The present invention also relates to prodrug derivatives of compounds of the present invention.

The present invention also relates to methods for the prevention or treatment of a wide variety of conditions or disorders, and particularly those disorders characterized by dysfunction of nicotinic cholinergic neurotransmission including disorders involving neuromodulation of neurotransmitter release, such as dopamine release. The present invention also relates to methods for the prevention or treatment of disorders, such as central nervous system (CNS) disorders, which are characterized by an alteration in normal neurotransmitter release. The present invention also relates to methods for the treatment of certain conditions (e.g., a method for alleviating pain). The methods involve administering to a subject an effective amount of a compound of the present invention.

The present invention, in another aspect, relates to a pharmaceutical composition comprising an effective amount of a compound of the present invention. Such a pharmaceutical composition incorporates a compound which, when employed in effective amounts, has the capability of interacting with relevant nicotinic receptor sites of a subject, and hence has the capability of acting as a therapeutic agent in the prevention or treatment of a wide variety of conditions and disorders, particularly those disorders characterized by an alteration in normal neurotransmitter release. Preferred pharmaceutical compositions comprise compounds of the present invention.

The pharmaceutical compositions of the present invention are useful for the prevention and treatment of disorders, such as CNS disorders, which are characterized by an alteration in normal neurotransmitter release. The pharmaceutical compositions provide therapeutic benefit to individuals suffering from such disorders and exhibiting clinical manifestations of such disorders in that the compounds within those compositions, when employed in effective amounts, have the potential to (i) exhibit nicotinic pharmacology and affect relevant nicotinic receptors sites (e.g., act as a pharmacological agonist to activate nicotinic receptors), and (ii) elicit neurotransmitter secretion, and hence prevent and suppress the symptoms associated with those diseases. In addition, the compounds are expected to have the potential to (i) increase the number of nicotinic cholinergic receptors of the brain of the patient, (ii) exhibit neuroprotective effects and (iii) when employed in effective amounts do not cause appreciable adverse side effects (e.g., significant increases in blood pressure and heart rate, significant negative effects upon the gastro-intestinal tract, and significant effects upon skeletal muscle). The pharmaceutical compositions of the present invention are believed to be safe and effective with regards to prevention and treatment of a wide variety of conditions and disorders.

The foregoing and other aspects of the present invention are explained in detail in the detailed description and examples set forth below.

DETAILED DESCRIPTION OF THE INVENTION

The compounds of the present invention include compounds of the formula:

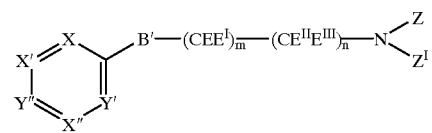

where each of X, X', X", Y' and Y" are individually nitrogen, nitrogen bonded to oxygen (e.g., an N-oxide (N—O) functionality) or carbon bonded to a substituent species characterized as having a sigma mn value greater than 0, often greater than 0.1, and generally greater than 0.2, and even greater than 0.3; less than 0 and generally less than −0.1; or 0; as determined in accordance with Hansch et al., Chem. Rev. 91:165 (1991). Preferably, less than 4, more preferably less than 3, and most preferably 1 or 2 of X, X', X", Y' and Y" are nitrogen, or nitrogen bonded to oxygen. In addition, it is highly preferred that not more than 1 of X, X', X", Y' and Y" be nitrogen bonded to oxygen; and it is preferred that if one of those species is nitrogen bonded to oxygen, that species is X". Typically, X' is CH, CBr or COR'. Typcially, X is CH. Most preferably, X" is nitrogen. In certain preferred circumstances, both X' and X" are nitrogen. Typically, Y' and Y" each are carbon bonded to a substituent species, and it is preferred that Y' and Y" both are carbon bonded to a substituent species such as hydrogen. In addition, m is an integer and n is an integer such that the sum of m plus n is 1, 2, 3, 4, 5 or 6, preferably is 1, 2, or 3, and most preferably is 2 or 3. It is highly preferred that m is 1 and n is 1. When any of X, X', X", Y' and Y" are carbon bonded to a substituent species, those substituent species often has a sigma m value between about −0.3 and about 0.75, frequently between about −0.25 and about 0.6; and each sigma m value individually can be 0 or not equal to zero.

B' is a substituted or unsubstituted two carbon atom bridging species and can be selected from the following:

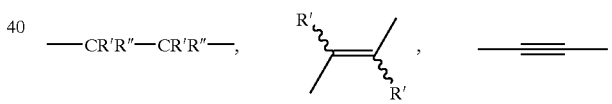

B' can be saturated or unsaturated (e.g., with R' and R") and can be part of a substituted or unsubstituted cycloalkyl ring (e.g., cyclopropyl, cyclobutyl, cyclopentyl, etc.). Substituents of B' (e.g., either R' or R") and the associated substituent species of X or Y" (i.e., when each relevant X and Y" are carbon atoms bonded to a substituent species), can combine to form a ring structure, such as a 5 or 6 membered ring structure (e.g., cycloalkyl, substituted cycloalkyl, heterocyclyl, substituted heterocyclyl). Typically, in such a circumstance, the substituent species of carbon atom of the bridging species immediately adjacent of aromatic ring combines with X or Y" to form such a ring. In addition, substituents of B', at least one of E, E$^I$, E$^{II}$ and E$^{III}$, and the intervening atoms, can combine to form monocyclic ring structures (e.g., cycloalkyl, substituted cycloalkyl, heterocyclyl, or substituted heterocyclyl structures) or bicyclic ring structures.

E, E$^I$, E$^{II}$ and E$^{III}$ individually represent hydrogen, alkyl (e.g., straight chain or branched alkyl including $C_1$–$C_8$, preferably $C_1$–$C_5$, such as methyl, ethyl, or isopropyl), substituted alkyl, halo substituted alkyl (e.g., straight chain or branched alkyl including $C_1$–$C_8$, preferably $C_1$–$C_5$, such as trifluoromethyl or trichloromethyl), cycloalkyl, substituted cycloalkyl, heterocyclyl, substituted heterocyclyl, aryl, substituted aryl, alkylaryl, substituted alkylaryl, arylalkyl or substituted arylalkyl; all of E, $E^I$, $E^{II}$, $E^{III}$ can be hydrogen, or at least one of E, $E^I$, $E^{II}$, $E^{III}$ is non-hydrogen (e.g., alkyl, substituted alkyl, halo substituted alkyl, cycloalkyl, substituted cycloalkyl, heterocyclyl, substituted heterocyclyl, aryl, substituted aryl, alkylaryl, substituted alkylaryl, arylalkyl or substituted arylalkyl) and the remaining E, $E^I$, $E^{II}$, $E^{III}$ are hydrogen; either E and $E^I$ or $E^{II}$ and $E^{III}$ and their associated carbon atom can combine to form a ring structure such as cyclopentyl, cyclohexyl or cycloheptyl; either E and $E^{II}$ or $E^I$ and $E^{III}$ and their associated carbon atoms can combine to form a ring structure such as cyclopentyl, cyclohexyl or cycloheptyl; Z and $Z^I$ individually represent hydrogen or alkyl (e.g., straight chain or branched alkyl including $C_1$–$C_8$, preferably $C_1$–$C_5$, such as methyl, ethyl, or isopropyl), and preferably at least one of Z and $Z^I$ is hydrogen, and most preferably Z is hydrogen and $Z^I$ is methyl; alternatively Z is hydrogen and $Z^I$ represents a ring structure (cycloalkyl, heterocyclyl, aryl or alkylaryl), such as cyclopropyl, cyclobutyl, cyclopentyl, cyclohexyl, cycloheptyl, adamantyl, quinuclidinyl, pyridinyl, quinolinyl, pyrimidinyl, phenyl, benzyl, thiazolyl or oxazolyl, methylpyridine, ethylpyridine, methylpyrazine or ethylpyrazine (where any of the foregoing can be suitably substituted with at least one substituent group, such as alkyl, alkoxyl, halo, or amino substituents); alternatively Z is hydrogen and $Z^I$ is propargyl; alternatively Z, $Z^I$, and the associated nitrogen atom can form a ring structure such as aziridinyl, azetidinyl, pyrollidinyl, piperidinyl, piperazinyl, morpholinyl, iminothiazolinyl or iminooxazolinyl (optionally substituted with pyridinyl, such as 3-pyridinyl, or pyrimidinyl, such as 5-pyrimidinyl); $Z^I$ and $E^I$ and the associated carbon and nitrogen atoms can combine to form a monocyclic ring structure such as pyrazolyl or isoxazalaminyl; $Z^I$ and $E^{III}$ and the associated carbon and nitrogen atoms can combine to form a monocyclic ring structure such as azetidinyl, pyrollidinyl, piperidinyl, thiazolyl, oxazolyl or piperazinyl or a bicyclic ring structure such as 3-([4.2.0]-2-azabicyclooctyl), 3-([2.2.2]-2-azabicyclooctyl), or 3-([2.2.1]-2-azabicycloheptyl); Z, $Z^I$ and $E^{III}$ and the associated carbon and nitrogen atoms can combine to form a bicyclic ring structure such as quinuclidinyl, 2-([2.2.1]-1-azabicycloheptyl), or 2-([3.3.0]-1-azabicyclooctyl), or a tricyclic ring structure such as azaadamantyl; $Z^I$, $E^{II}$ and $E^{III}$ and the associated carbon and nitrogen atoms can combine to form a bicyclic ring structure such as 1-([2.2.1]-2-azabicycloheptyl); Z, $Z^I$, $E^{II}$ and $E^{III}$ and the associated carbon and nitrogen atoms can combine to form a tricyclic ring structure. In the situation in which B' is olefinic and its associated $R^I$ substituent combines with X or $Y^I$ to form a 5 membered heterocyclic aromatic ring (e.g., furan, pyrrole or thiophene), combinations of Z, $Z^I$, E, $E^I$, $E^{II}$ and $E^{III}$ most preferably do not combine to form a ring structure; that is, in such a situation, Z and $Z^I$ most preferably are independently hydrogen or alkyl, and although much less preferred, Z and $Z^I$ can combine with the associated nitrogen atom only to form a ring structure. More specifically, X, X', X", Y' and Y" individually include N, N—O, or an aromatic carbon atom bearing one of the following substituent species: H, alkyl, substituted alkyl, alkenyl, substituted alkenyl, heterocyclyl, substituted heterocyclyl, cycloalkyl, substituted cycloalkyl, aryl, substituted aryl, alkylaryl, substituted alkylaryl, arylalkyl, substituted arylalkyl, F, Cl, Br, I, NR'R", $CF_3$, OH, CN, $NO_2$, $C_2R'$, SH, $SCH_3$, $N_3$, $SO_2CH_3$, OR', $(CR'R")_qOR'$, O—$(CR'R")_qC_2R'$, SR', C(=O)NR'R", NR'C(=O)R", C(=O)R', C(=O)OR', OC(=O)R', $(CR'R")_qOCH_2C_2R'$, $(CR'R")_qC(=O)R'$, $(CR'R")_qC(CHCH_3)OR'$, $O(CR'R")_qC(=O)OR'$, $(CR'R")_qC(=O)NR'R"$, $(CR'R")_qNR'R"$, CH=CHR', OC(=O)NR'R" and NR'C(=O)OR" where q is an integer from 1 to 6 and R' and R" are individually hydrogen, or alkyl (e.g., $C_1$–$C_{10}$ alkyl, preferably $C_1$–$C_5$ alkyl, and more preferably methyl, ethyl, isopropyl, tertiarybutyl, cycloalkyl, cyclopropyl, cyclobutyl, cyclopentyl, cyclohexyl, cycloheptyl or isobutyl), cycloalkyl (e.g., cyclopropyl cyclobutyl, cyclopentyl, cyclohexyl, cycloheptyl, and adamantyl), a non-aromatic heterocyclic ring wherein the heteroatom of the heterocyclic moiety is separated from any other nitrogen, oxygen or sulfur atom by at least two carbon atoms (e.g., quinuclidinyl, pyrollidinyl, and piperidinyl), an aromatic group-containing species (e.g., pyridyl, quinolinyl, pyrimidinyl, furanyl, phenyl, and benzyl where any of the foregoing can be suitably substituted with at least one substituent group, such as alkyl, alkoxyl, halo, or amino substituents). Other representative aromatic ring systems are set forth in Gibson et al., *J. Med. Chem.* 39:4065 (1996). R' and R" can be straight chain or branched alkyl, or R' and R" and the intervening atoms can combine to form a ring structure (e.g., cyclopropyl cyclobutyl, cyclopentyl, cyclohexyl, cycloheptyl, adamantyl or quinuclidinyl). Substituent species to the aromatic carbon atoms previously described for X, X', X", Y' and Y", when adjacent, can combine to form one or more saturated or unsaturated, substituted or unsubstituted carbocyclic or heterocyclic rings containing, but not limited to, ether, acetal, ketal, amine, ketone, lactone, lactam, carbamate, or urea functionalities. In addition, it is highly preferred that Y' is carbon bonded to hydrogen, and it is preferred that X is C—H. Preferably, E, $E^I$ and $E^{II}$ are hydrogen. In one preferred embodiment, n is 1, m is 1 or 2, E, $E^I$ and $E^{II}$ each are hydrogen, and $E^{III}$ is alkyl (e.g., methyl). In another preferred embodiment, n is 1, m is 1 or 2 and E, $E^I$, $E^{II}$, $E^{III}$ each are hydrogen. Depending upon the identity and positioning of each individual E, $E^I$, $E^{II}$ and $E^{III}$, certain compounds can be optically active. Additionally, compounds of the present invention can have chiral centers within the side chain (e.g., the compound can have an R or S configuration). Depending upon E, $E^I$, $E^{II}$ and $E^{III}$, compounds of the present invention have chiral centers, and the present invention relates to racemic mixtures of such compounds as well as enantiomeric compounds. Typically, the selection of n, m, E, $E^I$, $E^{II}$ and $E^{III}$ is such that up to about 4, and frequently up to 3, and usually 0, 1 or 2, of the substituents designated as E, $E^I$, $E^{II}$ and $E^{III}$ are non-hydrogen substituents (i.e., substituents such as alkyl or halo-substituted alkyl).

As employed herein, "alkyl" refers to straight chain or branched alkyl radicals including $C_1$–$C_8$, preferably $C_1$–$C_5$, such as methyl, ethyl, or isopropyl; "substituted alkyl" refers to alkyl radicals further bearing one or more substituent groups such as hydroxy, alkoxy, mercapto, aryl, heterocyclo, halo, amino, carboxyl, carbamyl, cyano, and the like; "alkenyl" refers to straight chain or branched hydrocarbon radicals including $C_1$–$C_8$, preferably $C_1$–$C_5$ and having at least one carbon-carbon double bond; "substituted alkenyl" refers to alkenyl radicals further bearing one or more substituent groups as defined above; "cycloalkyl" refers to saturated or unsaturated cyclic ring-containing radicals containing three to eight carbon atoms, preferably three to six carbon atoms; "substituted cycloalkyl" refers to cycloalkyl radicals further bearing one or more substituent groups as defined above; "aryl" refers to aromatic radicals having six to ten carbon atoms; "substituted aryl" refers to aryl radicals further bearing one or more substituent groups as defined above; "alkylaryl" refers to alkyl-substituted aryl radicals;

"substituted alkylaryl" refers to alkylaryl radicals further bearing one or more substituent groups as defined above; "arylalkyl" refers to aryl-substituted alkyl radicals; "substituted arylalkyl" refers to arylalkyl radicals further bearing one or more substituent groups as defined above; "heterocyclyl" refers to saturated or unsaturated cyclic radicals containing one or more heteroatoms (e.g., O, N, S) as part of the ring structure and having two to seven carbon atoms in the ring; and "substituted heterocyclyl" refers to heterocyclyl radicals further bearing one or more substituent groups as defined above.

Of particular interest are compounds of the formula:

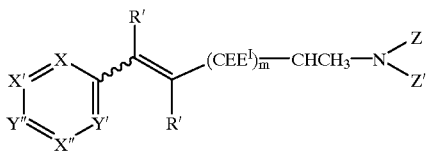

where X, X', X", Y', Y", E, $E^I$, Z, $Z^I$, m and R' are as defined hereinbefore. The wavy line in the structure indicates that the compound can have the cis (Z) or trans (E) form, preferably the trans (E) form. Preferably, both R' are hydrogen, or either or both of R' are methyl. Preferably, Z is hydrogen and $Z^I$ is hydrogen or methyl. Preferably, m is 1 or 2. Preferably, each E is hydrogen, and preferably each $E^I$ is hydrogen or methyl, but most preferably all of E and $E^I$ are hydrogen. Preferably, Y" is carbon bonded to a substituent species, and most preferably, that substituent species is hydrogen, halo, NR'R" or OR". Preferably, X" is nitrogen or carbon bonded to a substituent species such as NR'R", $NO_2$ or OR", but most preferably is nitrogen. Preferably, X' is nitrogen, but also preferably is carbon bonded to a substituent species such as hydrogen, R', halo, OR', NR'R", CN, $C_2$R' or CHCHR'. Preferably, X is carbon bonded to a substituent species, such as hydrogen.

Representative compounds of the present invention include (3E)-N-methyl-4-[3-(5-nitro-6-aminopyridin)yl]-3-buten-1-amine, (3E)-N-methyl-4-[3-(5-(N-benzylcarboxamido)pyridin)yl]-3-buten-1-amine, (4E)-N-methyl-5-[5-(2-aminopyrimidin)yl]-4-penten-2-amine, (4E)-N-methyl-5-(3-(5-aminopyridin)yl)-4-penten-2-amine, (2S)-(4E)-N-methyl-5-[3-(5-isopropoxy-1-oxopyridin)yl)]-4-penten-2-amine, (3E)-N-rmethyl-4-(3-(5-isobutoxypyridin)yl)-3-buten-1-amine, (3E)-N-methyl-4-(3-(1-oxopyridin)yl)-3-buten-1-amine, (4E)-N-methyl-5-(3-(1-oxopyridin)yl)-4-penten-2-amine, (3E)-N-methyl-4-(3-(5-ethylthiopyridin)yl)-3-buten-1-amine, (4E)-N-methyl-5-(3-(5-trifluoromethylpyridin)yl)-4-penten-2-amine, (4E)-N-methyl-5-(3-(5-((carboxymethyl)oxy)pyridin)yl)-4-penten-2-amine, (4E)-5-(3-(5-isopropoxypyridin)yl)-4-penten-2-amine, and (4E)-N-methyl-5-(3-(5-hydroxypyridin)yl)-4-penten-2-amine.

The following compounds also are representative compounds of the present invention: 4-(N-methylamino)-1-(3-(5-isopropoxypyridin)yl)-1-pentan-1-ol, (2R)-(4E)-N-methyl-5-(5-pyrimidinyl)-4-penten-2-amine, (2S)-(4E)-N-methyl-5-(5-pyrimidinyl)-4-penten-2-amine, (2R)-(4E)-N-methyl-5-[3-(5-methoxypyridin)yl]-4-penten-2-amine, (2S)-(4E)-N-methyl-5-[3-(5-methoxypyridin)yl]-4-penten-2-amine, (4E)-N-methyl-5-[3-(5-cyclopentyloxypyridin)yl]-4-penten-2-amine, (4E)-N-methyl-5-[3-(5-cyclohexyloxypyridin)yl]-4-penten-2-amine, (4E)-N-methyl-5-[3-(5-cyanopyridin)yl]-4-penten-2-amine, (4E)-N-methyl-5-[3-(5-ethynylpyridin)yl]-4-penten-2-amine, (4E)-N-methyl-5-[3-(5-phenylethynylpyridin)yl]-4-penten-2-amine, (4E)-N-methyl-5-[3-(5-(4-methoxyphenylethynyl)pyridin)yl]-4-penten-2-amine, (4E)-N-methyl-5-[3-(5-trans-beta-styrylpyridin)yl]-4-penten-2-amine, (4E)-N-methyl-5-[3-(6-methoxypyridin)yl]-4-penten-2-amine, (4E)-N-methyl-5-[3-(5-phenylpyridin)yl]-4-penten-2-amine, (4B)-N-methyl-5-[3-(5-(4-methoxyphenyl)pyridin)yl]-4-penten-2-amine, (4E)-N-methyl-5-[3-(5-(4-hydroxyphenyl)pyridin)yl]-4-penten-2-amine, (4E)-N-methyl-5-[3-(5-(4-fluorophenylpyridin)yl]-4-penten-2-amine, (4E)-N-methyl-5-[3-(5-(3,4-methylenedioxyphenylpyridin)yl]-4-penten-2-amine, (4E)-N-methyl-5-[3-(5-phenoxypyridin)yl]-4-penten-2-amine, (4E)-N-methyl-5-[3-(5-(4-methoxyphenoxy)pyridin)yl]-4-penten-2-amine, (4E)-N-methyl-5-[3-(5-(4-hydroxyphenoxy)pyridin)yl]-4-penten-2-amine, (4E)-N-methyl-5-[3-(5-(4-fluorophenoxy)pyridin)yl]-4-penten-2-amine, (4E)-N-methyl-5-[3-(5-(3,4-methylenedioxyphenoxy)pyridin)yl]-4-penten-2-amine, (4E)-N-methyl-5-[3-(5-benzyloxypyridin)yl]-4-penten-2-amine, 4E)-N-methyl-5-[3-(5-(4-methoxybenxyoxy) pyridin)yl]-4-penten-2-amine, 4E)-N-methyl-5-[3-(5-(4-hydroxybenzyloxy)pyridin)yl]-4-penten-2-amine, 4E)-N-methyl-5-[3-(5-(4-fluorobenzyloxy)pyridin )yl]-4-penten-2-amine, and 4E)-N-methyl-5-[3-(5-(3,4-methlenedioxybenzyloxy)pyridin)yl]-4-penten-2-amine.

Yet other representative compounds of the present invention include the following: (1-methyl-4-(3-pyridyl)but-3-enyl)(3-pyridylmethyl)amine, methyl(1-methyl-4-(2-(prop-2-ynyloxymehtyl)pyrimidin-5yl)but-3-enyl)amine and methyl(1-methyl-4-(2-(2-phenylvinyl)pyrimidin-5-yl)but-3-enyl)amine.

The manner in which aryl substituted olefinic amine compounds of the present invention are synthetically produced can vary. Exemplary techniques and procedures for providing compounds of the present invention are set forth in U.S. Pat. No. 5,616,716 to Dull et al. and U.S. patent application Ser. No. 09/098,285, filed Jun. 16, 1998, which are incorporated herein by reference in their entirety.

(E)-metanicotine-type compounds can be prepared using the techniques set forth by Löffler et al., Chem. Ber., 42, pp. 3431–3438 (1909) and Laforge, J.A.C.S., 50, p. 2477 (1928) from substituted nicotine-type compounds. Certain 6-substituted metanicotine-type compounds can be prepared from the corresponding 6-substituted nicotine-type compounds using the general methods of Acheson et al., J. Chem. Soc., Perkin Trans. 1, 2, pp. 579–585 (1980). The requisite precursors for such compounds, 6-substituted nicotine-type compounds, can be synthesized from 6-substituted nicotinic acid esters using the general methods disclosed by Rondahl, Acta Pharm. Suec., 14, pp 113–118 (1977). Preparation of certain 5-substituted metanicotine-type compounds can be accomplished from the corresponding 5-substituted nicotine-type compounds using the general method taught by Acheson et al., J. Chem. Soc., Perkin Trans. 1, 2, pp. 579–585 (1980). The 5-halo-substituted nicotine-type compounds (e.g., fluoro- and bromo-substituted nicotine-type compounds) and the 5-amino nicotine-type compounds can be prepared using the general procedures disclosed by Rondahl, Act. Pharm. Suec., 14, pp.113–118 (1977). The 5-trifluoromethyl nicotine-type compounds can be prepared using the techniques and materials set forth in Ashimori et al., Chem. Pharm. Bull., 38(9), pp. 2446–2458 (1990) and Rondahl, Acta Pharm. Suec., 14, pp.1 13–118 (1977).

Furthermore, preparation of certain metanicotine-type compounds can be accomplished using a palladium catalyzed coupling reaction of an aromatic halide and a terminal olefin containing a protected amine substituent, removal of the protective group to obtain a primary amine, and optional alkylation to provide a secondary or tertiary amine. In particular, certain metanicotine-type compounds can be prepared by subjecting a 3-halo-substituted, 5-substituted pyridine compound or a 5-halo-substituted pyrimidine compound to a palladium catalyzed coupling reaction using an olefin possessing a protected amine functionality (e.g., such an olefin provided by the reaction of a phthalimide salt with 3-halo-1-propene, 4-halo-1-butene, 5-halo-1-pentene or 6-halo-1-hexene). See, Frank et al., J. Org. Chem., 43(15), pp. 2947–2949 (1978) and Malek et al., J. Org. Chem., 47, pp. 5395–5397 (1982). Alternatively, certain metanicotine-type compounds can be prepared by coupling an N-protected, modified amino acid residue, such as 4-(N-methyl-N-tert-butyloxycarbonyl)aminobutyric acid methyl ester, with an aryl lithium compound, as can be derived from a suitable aryl halide and butyl lithium. The resulting N-protected aryl ketone is then chemically reduced to the corresponding alcohol, converted to the alkyl halide, and subsequently dehydrohalogenated to introduce the olefin functionality. Removal of the N-protecting group then affords the desired metanicotine-type compound.

There are a number of different methods for providing (Z)-metanicotine-type compounds. In one method, (Z)-metanicotine-type compounds can be synthesized from nicotine-type compounds as a mixture of E and Z isomers; and the (Z)-metanicotine-type compounds can then be separated by chromatography using the types of techniques disclosed by Sprouse et al., Abstracts of Papers, p. 32, Coresta/TCRC Joint Conference (1972). In another method, metanicotine-type compounds can be prepared by the controlled hydrogenation of the corresponding acetylenic compound (e.g., an N-methyl-4-(3-pyridinyl)-3-butyn-1-amine type compound). For example, certain 5-substituted (Z)-metanicotine-type compounds and certain 6-substituted (Z)-metanicotine-type compounds can be prepared from 5-substituted-3-pyridinecarboxaldehydes and 6-substituted-3-pyridinecarboxaldehydes, respectively. Representative synthetic techniques for (Z)-metanicotine-type compounds are set forth in U.S. Pat. No. 5,597,919 to Dull et al. the disclosure of which is incorporated herein in its entirety.

There are a number of methods by which the (Z)-olefinic isomers of aryl substituted olefinic amine compounds can be synthetically produced. In one approach, the (Z)-isomers of aryl substituted olefinic amine compounds can be prepared by the controlled hydrogenation of the corresponding alkynyl compounds (e.g., a N-methyl-5-(3-pyridyl)-4-butyn-2-amine-type compound) using commercially available Lindlar catalyst (Aldrich Chemical Company) using the methodology set forth in H. Lindlar et al., Org. Syn. 46: 89 (1966). The requisite alkynyl compounds can be prepared by the palladium catalyzed coupling of an aromatic halide, preferably a 3-bromopyridine-type or a 3-iodopyridine-type compound with an alkynyl side chain compound (e.g., an N-methyl-4-pentyn-2-amine-type compound). Typically the methodolgy set forth in L. Bleicher et al., Synlett. 1115 (1995) is used for the palladium catalyzed coupling of an aryl halide with a monosubstituted alkyne in the presence of copper(I) iodide and triphenylphosphine and potassium carbonate as a base. Alkynyl compounds such as N-methyl-4-pentyn-2-amine can be prepared from commercially available 4-pentyn-2-ol (Aldrich Chemical Company) by treatment with p-toluenesulfonyl chloride in pyridine, followed by reaction of the resulting 4-pentyn-2-ol p-toluenesulfonate with excess methylamine either as a 40% aqueous solution or as a 2.0 M solution in tetrahydrofuran. In some instances it may be necessary to protect the amino functionality of the N-methyl-4-pentyn-2-amine-type compound by treatment with di-tert-butyl dicarbonate to give the tert-butoxycarbonyl protected amine-type compound. Such protected amine compounds may undergo the palladium catalyzed coupling with aryl halides and the subsequent controlled hydrogenation of the resulting alkynyl compound more easily than the unprotected amine compounds. The tert-butoxycarbonyl protecting group can be easily removed using a strong acid such as trifluoroacetic acid to yield the (Z)-olefinic isomers of aryl substituted olefinic amine compounds.

The methods by which aryl substituted olefinic amine compounds of the present invention can be synthetically produced can vary. An olefinic alcohol, such as 4-penten-2-ol, is condensed with an aromatic halide, such as 3-bromopyridine or 3-iodopyridine. Typically, the types of procedures set forth in Frank et al., J. Org. Chem., 43, pp. 2947–2949 (1978) and Malek et al., J. Org. Chem., 47, pp. 5395–5397 (1982) involving a palladium-catalyzed coupling of an olefin and an aromatic halide are used. The olefinic alcohol optionally can be protected as a t-butyldimethylsilyl ether prior to the coupling. Desilylation then produces the olefinic alcohol. The alcohol condensation product then is converted to an amine using the type of procedures set forth in deCosta et al., J. Org. Chem., 35, pp. 4334–4343 (1992). Typically, the alcohol condensation product is converted to the aryl substituted olefinic amine by activation of the alcohol using methanesulfonyl chloride or p-toluenesulfonyl chloride, followed by mesylate or tosylate displacement using ammonia, or a primary or secondary amine. Thus, when the amine is ammonia, an aryl substituted olefinic primary amine compound is provided; when the amine is a primary amine such as methylamine or cyclobutylamine, an aryl substituted olefinic secondary amine compound is provided; and when the amine is a secondary amine such as dimethylamine or pyrrolidine, an aryl substituted olefinic tertiary amine compound is provided. Other representative olefinic alcohols include 4-penten-1-ol, 5-hexen-2-ol, 5-hexen-3-ol, 3-methyl-3-buten-1-ol, 2-methyl-3-buten-1-ol, 4-methyl-4-penten-1-ol, 4-methyl-4-penten-2-ol, 1-octen-4-ol, 5-methyl-1-hepten-4-ol, 4-methyl-5-hexen-2-ol, 5-methyl-5-hexen-2-ol, 5-hexen-2-ol and 5-methyl-5-hexen-3-ol. Trifluormethyl-substituted olefinic alcohols, such as 1,1,1-trifluoro-4-penten-2-ol, can be prepared from 1-ethoxy-2,2,2-trifluoro-ethanol and allyl-trimethylsilane using the procedures of Kubota et al., Tetrahedron Letters, Vol. 33(10), pp. 1351–1354 (1992), or from trifluoroacetic acid ethyl ester and allyltributylstannane using the procedures of Ishihara et al., Tetrahedron Letters, Vol. 34(56), pp. 5777–5780 (1993). Certain olefinic alcohols are optically active, and can be used as enantiomeric mixtures or as pure enantiomers in order to provide the corresponding optically active forms of aryl substituted olefinic amine compounds. When an olefinic allylic alcohol, such as methallyl alcohol, is reacted with an aromatic halide, an aryl substituted olefinic aldehyde is produced; and the resulting aldehyde can be converted to an aryl substituted olefinic amine compound by reductive amination (e.g., by treatment using an alkyl amine and sodium cyanoborohydride). Preferred aromatic halides are 3-bromopyridine-type compounds and 3-iodopyridine-type compounds. Typically, substituent groups of such 3-halopyridine-type compounds are such that those groups can survive contact with those chemicals (e.g., tosylchloride and methylamine) and the reaction conditions experienced during the preparation of the aryl substituted olefinic amine compound. Alternatively, substituents such as —OH, —NH$_2$ and —SH can be protected as corresponding acyl compounds, or substituents such as —NH$_2$ can be protected as a phthalimide functionality. In the case of a dihaloaromatic, sequential palladium-catalyzed (Heck-type) couplings to two different olefinic side chains are possible.

The manner in which certain aryl substituted olefinic amine compounds possessing a branched side chain, such as (4E)-N-methyl-5-(5-isopropoxy-3-pyridyl)-4-penten-2-amine, are provided can vary. By using one synthetic approach, the latter compound can be synthesized in a convergent manner, in which the side chain, N-methyl-N-(tert-butoxycarbonyl)-4-penten-2-amine is coupled with the 3-substituted 5-halo-substituted pyridine, 5-bromo-3-isopropoxypyridine, under Heck reaction conditions, followed by removal of the tert-butoxycarbonyl protecting group. Typically, the types of procedures set forth in W. C. Frank et al., *J. Org Chem.* 43: 2947 (1978) and N. J. Malek et al., *J. Org. Chem.* 47: 5395 (1982) involving a palladium-catalyzed coupling of an olefin and an aromatic halide are used. The required N-methyl-N-(tert-butoxycarbonyl)-4-penten-2-amine can be synthesized as follows: (i) Commercially available 4-penten-2-ol (Aldrich Chemical Company, Lancaster Synthesis Inc.) can be treated with p-toluenesulfonyl chloride in pyridine to yield 4-penten-2-ol p-toluenesulfonate, previously described by T. Michel, et al., *Liebigs Ann.* 11: 1811 (1996). (ii) The resulting tosylate can be heated with 20 molar equivalents of methylamine as a 40% aqueous solution to yield N-methyl-4-penten-2-amine. (iii) The resulting amine, such as previously mentioned by A. Viola et al., *J. Chem. Soc., Chem. Commun.* (21): 1429 (1984), can be allowed to react with 1.2 molar equivalents of di-tert-butyl dicarbonate in dry tetrahydrofuran to yield the side chain, N-methyl-N-(tert-butoxycarbonyl)-4-penten-2-amine. The halo-substituted pyridine, (e.g., 5-bromo-3-isopropoxypyridine) can be synthesized by two different routes. In one preparation, 3,5-dibromopyridine is heated at 140° C. for 14 hours with 2 molar equivalents of potassium isopropoxide in dry isopropanol in the presence of copper powder (5%, w/w of the 3,5-dibromopyridine) in a sealed glass tube to yield 5-bromo-3-isopropoxypyridine. A second preparation of 5-bromo-3-isopropoxypyridine from 5-bromonicotinic acid can be performed as follows: (i) 5-Bromonicotinic acid is converted to 5-bromonicotinamide by treatment with thionyl chloride, followed by reaction of the intermediate acid chloride with aqueous ammonia. (ii) The resulting 5-bromonicotinamide, previously described by C. V. Greco et al., *J. Heteocyclic Chem.* 7(4): 761 (1970), is subjected to Hofmann degradation by treatment with sodium hydroxide and a 70% solution of calcium hypochlorite. (iii) The resulting 3-amino-5-bromopyridine, previously described by C. V. Greco et al., *J. Heteocyclic Chem.* 7(4): 761 (1970), can be converted to 5-bromo-3-isopropoxypyridine by diazotization with isoamyl nitrite under acidic conditions, followed by treatment of the intermediate diazonium salt with isopropanol to yield 5-bromo-3-isopropoxypyridine. The palladium-catalyzed coupling of 5-bromo-3-isopropoxypyridine and N-methyl-N-(tert-butoxycarbonyl)-4-penten-2-amine is carried out in acetonitrile-triethylamine (2:1, v,v) using a catalyst consisting of 1 mole % palladium(II) acetate and 4 mole % tri-o-tolylphosphine. The reaction can be carried out by heating the components at 80° C. for 20 hours to yield (4E)-N-methyl-N-(tert-butoxycarbonyl)-5-(5-isopropoxy-3-pyridyl)-4-penten-2-amine. Removal of the tert-butoxycarbonyl protecting group can be accomplished by treatment with 30 molar equivalents of trifluoroacetic acid in anisole at 0° C. to afford (4E)-N-methyl-5-(5-isopropoxy-3-pyridyl)-4-penten-2-amine. A variety of N-methyl-5-(5-alkoxy or 5-aryloxy-3-pyridyl)-4-penten-2-amines are available from 3,5-dibromopyridine using this type of technology (i.e., treatment with sodium or potassium alkoxides or aryloxides and subsequent Heck coupling and deprotection).

The manner in which certain aryl substituted olefinic amine compounds possessing a branched side chain are provided can vary. Using one synthetic approach, a compound such as (4E)-N-methyl-5-(5-methoxy-3-pyridyl)-4-penten-2-amine can be synthesized by coupling a halo-substituted pyridine, 5-bromo-3-methoxypyridine with an olefin containing a secondary alcohol functionality, 4-penten-2-ol, under Heck reaction conditions; and the resulting pyridyl alcohol intermediate can be converted to its p-toluenesulfonate ester, followed by treatment with methylamine. Typically, the types of procedures set forth in W. C. Frank et al., *J. Org. Chem.* 43: 2947 (1978) and N. J. Malek et al., *J. Org. Chem.* 47: 5395 (1982) involving a palladium-catalyzed coupling of an olefin and an aromatic halide are used. The required halo-substituted pyridine, 5-bromo-3-methoxypyridine is synthesized using methodology similar to that described by H. J. den Hertog et al., *Recl. Trav. Chim. Pays-Bas* 67:377 (1948), namely by heating 3,5-dibromopyridine with 2.5 molar equivalents of sodium methoxide in dry methanol in the presence of copper powder (5%, w/w of the 3,5-dibromopyridine) in a sealed glass tube at 150° C. for 14 hours to produce 5-bromo-3-methoxypyridine. The resulting 5-bromo-3-methoxypyridine, previously described by D. L. Comins, et al., *J. Org. Chem.* 55: 69 (1990), can be coupled with 4-penten-2-ol in acetonitrile-triethylamine (1:1:1, v/v) using a catalyst consisting of 1 mole % palladium(II) acetate and 4 mole % tri-o-tolylphosphine. The reaction is carried out by heating the components in a sealed glass tube at 140° C. for 14 hours to yield (4E)-N-methyl-5-(5-methoxy-3-pyridyl)-4-penten-2-ol. The resulting alcohol is treated with 2 molar equivalents of p-toluenesulfonyl chloride in dry pyridine at 0° C. to produce (4E)-N-methyl-5-(5-methoxy-3-pyridyl)-4-penten-2-ol p-toluensulfonate. The tosylate intermediate is treated with 120-molar equivalents of methylamine as a 40% aqueous solution, containing a small amount of ethanol as a co-solvent to produce (4E)-N-methyl-5-(5-methoxy-3-pyridyl)-4-penten-2-amine. When 3,5-dibromopyridine is submitted to Heck coupling with N-methyl-N-(tert-butoxycarbonyl)-4-penten-2-amine, under conditions described above, N-methyl-N-(tert-butoxycarbonyl)-5-(5-bromo-3-pyridyl)-4-penten-2-amine is produced. This can be coupled in a subsequent Heck reaction with styrene and deprotected (removal of the tert-butoxycarbonyl group), as described previously, to give (4E)-N-methyl-5-[3-(5-trans-beta-styrylpyridin)yl]-4-penten-2-amine. Similar second coupling with ethynylbenzene, and subsequent deprotection, will give (4E)-N-methyl-5-[3-(5-phenylethynylpyridin)yl]-4-penten-2-amine.

The manner in which optically active forms of certain aryl substituted olefinic amine compounds, such as (2S)-(4E)-N-methyl-5-(3-pyridyl)-4-penten-2-amine, are provided can vary. In one synthetic approach, the latter type of compound is synthesized by coupling a halo-substituted pyridine, 3-bromopyridine, with an olefin possessing a chiral, secondary alcohol functionality, (2R)-4-penten-2-ol, under Heck reaction conditions. The resulting chiral pyridyl alcohol intermediate, (2R)-(4E)-5-(3-pyridyl)-4-penten-2-ol is converted to its corresponding p-toluenesulfonate ester, which is subsequently treated with methylamine, resulting in tosylate displacement with inversion of configuration. Typically, the types of procedures set forth in W. C. Frank et al., *J. Org.*

*Chem.* 43: 2947 (1978) and N. J. Malek et al., *J. Org. Chem.* 47: 5395 (1982) involving a palladium-catalyzed coupling of an aromatic halide and an olefin are used. The chiral side chain, (2R)-4-penten-2-ol can be prepared by treatment of the chiral epoxide, (R)-(+)-propylene oxide (commercially available from Fluka Chemical Company) with vinylmagnesium bromide in tetrahydrofuran at low temperatures (−25 to −10° C.) using the general synthetic methodology of A. Kalivretenos, J. K. Stille, and L. S. Hegedus, *J. Org. Chem.* 56: 2883 (1991), to afford (2R)-4-penten-2-ol. The resulting chiral alcohol is subjected to a Heck reaction with 3-bromopyridine in acetonitrile-triethylamine (1:1, v/v) using a catalyst consisting of 1 mole % palladium(II) acetate and 4 mole % tri-o-tolylphosphine. The reaction is done by heating the components at 140° C. for 14 hours in a sealed glass tube, to produce the Heck reaction product, (2R)-(4E)-5-(3-pyridyl)-4-penten-2-ol. The resulting chiral pyridyl alcohol is treated with 3 molar equivalents of p-toluenesulfonyl chloride in dry pyridine at 0° C., to afford the tosylate intermediate. The p-toluenesulfonate ester is heated with 82 molar equivalents of methylamine as a 40% aqueous solution, containing a small amount of ethanol as a co-solvent, to produce (2S)-(4E)-N-methyl-5-(3-pyridyl)-4-penten-2-amine.

In a similar manner, the corresponding aryl substituted olefinic amine enantiomer, such as (2R)-(4E)-N-methyl-5-(3-pyridyl)-4-penten-2-amine, can be synthesized by the Heck coupling of 3-bromopyridine and (2S)-4-penten-2-ol. The resulting intermediate, (2S)-(4E)-5-(3-pyridyl)-4-penten-2-ol, is converted to its p-toluenesulfonate, which is subjected to methylamine displacement. The chiral alcohol, (2S)-4-penten-2-ol, is prepared from (S)-(−)-propylene oxide (commercially available from Aldrich Chemical Company) using a procedure analogous to that described for the preparation of (2R)-4-penten-2-ol from (R)-(+)-propylene oxide as reported by A. Kalivretenos, J. K. Stille, and L. S. Hegedus, *J. Org. Chem.* 56: 2883 (1991).

In another approach to compounds of the present invention, such compounds as (3E)-N-methyl-4-(3-(6-aminopyridin)yl)-3-buten-1-amine can be prepared by subjecting a 3-halo-substituted pyridine such as 2-amino-5-bromopyridine (Aldrich Chemical Company) to a palladium-catalyzed coupling reaction with an olefin possessing a protected amine functionality, such as N-methyl-N-(3-buten-1-yl)benzamide. Removal of the benzoyl-protecting group from the resulting Heck reaction product can be accomplished by heating with aqueous acid to give (3E)-N-methyl-4-(3-(6-aminopyridin)yl)-3-buten-1-amine. The required olefin, N-methyl-N-(3-buten-1-yl)benzamide, can be prepared by reacting 4-bromo-1-butene with an excess of condensed methylamine in N,N-dimethylformamide in the presence of potassium carbonate to give N-methyl-3-buten-1-amine. Treatment of the latter compound with benzoyl chloride in dichloromethane containing triethylamine affords the olefinic side chain, N-methyl-N-(3-buten-1-yl)benzamide.

Compounds of the present invention may contain an azacyclic functionality, such as pyrrolidine or quinuclidine. The methods of synthesis of such compounds may vary. In one method, the Heck reaction can be used for the coupling a vinyl-substituted or allyl-substituted nitrogen heterocycle to a 3-halopyridine. For example, N-(tert-butoxycarbonyl)-2-allylpyrrolidine and 3-bromopyridine (Aldrich Chemical Company) can be coupled under conditions described by W. C. Frank et al., *J. Org. Chem.* 43: 2947 (1978) and N. J. Malek et al., *J. Org. Chem.* 47: 5395 (1982) involving palladium catalysis. Removal of the protecting group, using trifluoroacetic acid, will give 2-(3-(3-pyridyl)-(2E)-propen-1-yl)pyrrolidine. The requisite N-(tert-butoxycarbonyl)-2-allylpyrrolidine can be prepared from commercially available 2-pyrrolidinemethanol (Aldrich Chemical Company). Treatment of 2-pyrrolidinemethanol with di-tert-butyl dicarbonate results in protection of the amine as its tert-butoxycarbonyl derivative. Subsequent reaction with p-toluenesulfonyl chloride in pyridine, followed by sodium iodide in acetone, gives 2-(iodomethyl)-N-(tert-butoxycarbonyl)pyrrolidine. This compound can be coupled with vinylmagnesium bromide in the presence of cuprous iodide to give N-(tert-butoxycarbonyl)-2-allylpyrrolidine. The use of enantiomerically pure 2-pyrrolidinemethanol (both R and S isomers are available from Aldrich Chemical Company) results in the preparation of each enantiomer of N-(tert-butoxycarbonyl)-2-allylpyrrolidine. Subsequent reactions as outlined above results in the preparation of each enantiomer of 2-(3-(3-pyridyl)-(2E)-propen-1-yl) pyrrolidine. The secondary amino compounds can be N-methylated using aqueous formaldehyde and sodium cyanoborohydride using methodology similar to that described by M. A. Abreo et al., *J. Med. Chem.* 39:817–825 (1996) to afford each enantiomer of 2-(3-(3-pyridyl)-(2E)-propen-1-yl)-1-methylpyrrolidine.

Similarly, 2-allylquinuclidine can be coupled with 3-bromopyridine, under Heck conditions, to give 2-(3-(3-pyridyl)-(2E)-propen-1-yl)quinuclidine. The required 2-allylquinuclidine can be prepared from 3-quinuclidinone (Aldrich Chemical Company) by alkylation and deoxygenation. Thus, 3-quinuclidinone can be converted into its isopropylimine with isopropylamine and molecular sieves. Treatment of the imine with lithium diisopropylamide and allyl bromide, followed by hydrolysis, gives 2-allyl-3-quinuclidinone. Deoxygenation, by conversion of the ketone into its p-toluenesulfonylhydrazone and reduction with sodium borohydride, gives 2-allylquinuclidine.

Compounds of the present invention may contain a pyrazine or pyridazine ring. Using procedures reported M. Hasegawa, et al. (European Patent Application 561409 A2 921202), 2-methylpyrazine or 3-methylpyridazine (both available from Aldrich Chemical Company) can be condensed with N-methyl-N-(tert-butoxycarbonyl)-3-aminobutanal to give (4E)-N-methyl-N-(tert-butoxycarbonyl)-5-(2-pyrazinyl)-4-penten-2-amine and (4E)-N-methyl-N-(tert-butoxycarbonyl)-5-(3-pyridazinyl)-4-penten-2-amine respectively. Removal of the tert-butoxycarbonyl group with trifluoroacetic acid will produce (4E)-N-methyl-5-(2-pyrazinyl)-4-penten-2-amine and (4E)-N-methyl-5-(3-pyridazinyl)-4-penten-2-amine respectively. The requisite N-methyl-N-(tert-butoxycarbonyl)-3-aminobutanal can be produced from the corresponding alcohol using techniques described by M. Adamczyk and Y. Y. Chen in PCT International Application WO 9212122. The alcohol, N-methyl-N-(tert-butoxycarbonyl)-3-amino-1-butanol, can be made from commercially available 4-hydroxy-2-butanone (Lancaster Synthesis, Inc.) by sequential reductive amination (with methylamine and sodium cyanoborohydride, using chemistry reported by R. F. Borch in *Org. Syn.* 52, 124 (1974)) and protection with di-tert-butyl dicarbonate.

The manner in which certain compounds of the present invention are prepared can vary. For example, compounds that possess certain fused-ring heterocycles can be prepared by the Heck reaction. Such compounds can be synthesized by the palladium-catalyzed coupling of a bromo heterocyclic compound, such as 6-bromo-2-methyl-1H-imidazo[4,5-b] pyridine with the previously mentioned olefinic amine side chain, N-methyl-N-(tert-butoxycarbonyl)-4-penten-2-amine. Typically, the types of procedures set forth in W. C. Frank et al., *J. Org. Chem.* 43: 2947 (1978) and N. J. Malek et al., *J. Org. Chem.* 47: 5395 (1982) involving a palladium-catalyzed coupling of an olefin and an aromatic halide are used for the coupling reaction. The resulting tert-butoxycarbonyl-protected (Boc-protected) intermediate can be subjected to treatment with a strong acid, such as trifluoroacetic acid to produce (4E)-N-methyl-5-(6-(2-methyl-1H-imidazo[4,5-b]pyridin)yl)-4-penten-2-amine. The requisite bromo-imidazopyridine, 6-bromo-2-methyl-1H-imidazo[4,5-b]pyridine can be prepared in 82% yield by heating 2,3-diamino-5-bromopyridine with acetic acid in polyphosphoric acid according to the methods described by P. K. Dubey et al., *Indian J Chem.* 16B(6):531–533 (1978). 2,3-Diamino-5-bromopyridine can be prepared in 97% yield by heating 2-amino-5-bromo-3-nitropyridine (commercially available from Aldrich Chemical Company and Lancaster Synthesis, Inc) with tin(II) chloride dihydrate in boiling ethanol according to the techniques described by S. X. Cai et al., *J. Med. Chem.* 40(22): 3679–3686 (1997).

In another example, a bromo fused-ring heterocycle, such as 6-bromo-1,3-dioxolo[4,5-b]pyridine can be coupled with the previously mentioned olefinic amine side chain, N-methyl-N-(tert-butoxycarbonyl)-4-penten-2-amine using the Heck reaction. The resulting Boc-protected intermediate can be deprotected with a strong acid such as trifluoroacetic acid to produce (4E)-N-methyl-5-(6-(1,3-dioxolo[4,5-b]pyridin)yl)-4-penten-2-amine. The requisite bromo compound, 6-bromo-1,3-dioxolo[4,5-b]pyridine can be synthesized from 5-bromo-2,3-dihydroxypyridine, also known as 5-bromo-3-hydroxy-2(1H)-pyridinone, via a methylenation procedure using bromochloromethane, in the presence of potassium carbonate and N,N-dimethylformamide according to the methodology of F. Dallacker et al., *Z. Naturforsch.* 34 b:1729–1736 (1979). 5-Bromo-2,3-dihydroxypyridine can be prepared from furfural (2-furaldehyde, commercially available from Aldrich Chemical Company and Lancaster Synthesis, Inc) using the methods described in F. Dallacker et al., *Z. Naturforsch.* 34 b:1729–1736 (1979). Alternatively, 5-bromo-2,3-dihydroxypyridine can be prepared according to the techniques described in EP 0081745 to D. Rose and N. Maak.

In an another example of a compound that possesses a fused-ring heterocycle, the bromo compound, 7-bromo-2,3-dihydro-1,4-dioxino[2,3-b]pyridine (also known as 7-bromo-5-aza-4-oxachromane) can be condensed with the previously mentioned olefinic amine side chain, N-methyl-N-(tert-butoxycarbonyl)-4-penten-2-amine using the Heck reaction. The resulting Boc-protected compound can be deprotected with strong acid such as trifluoroacetic acid to produce (4E)-N-methyl-5-(7-(2,3-dihydro-1,4-dioxino[2,3-b]pyridin)yl-4-penten-2-amine. The required bromo compound, 7-bromo-2,3-dihydro-1,4-dioxino[2,3-b]pyridine, can be prepared by treating 5-bromo-2,3-dihydroxypyridine with 1,2-dibromoethane and potassium carbonate in N,N-dimethylformamide according to the methodology of F. Dallacker et al., *Z. Naturforsch.* 34 b:1729–1736 (1979). 5-Bromo-2,3-dihydroxypyridine can be prepared from furfural as described above.

Other polycyclic aromatic compounds of the present invention can be prepared by the Heck reaction. Thus, certain compounds can be synthesized by the palladium-catalyzed coupling of a bromo fused-ring heterocycle, such as 6-bromo-1H-imidazo[4,5-b]pyridine-2-thiol with the previously mentioned olefinic amine side chain, N-methyl-N-(tert-butoxycarbonyl)-4-penten-2-amine. The Boc-protected intermediate, resulting from the Heck reaction, can be subjected to treatment with a strong acid, such as trifluoroacetic acid to produce (4E)-N-methyl-5-(6-(2-thio-1H-imidazo[4,5-b]pyridin)yl)-4-penten-2-amine. The requisite bromo compound, 6-bromo-1H-imidazo[4,5-b]pyridine-2-thiol can be prepared by treating 6-bromo-1H-imidazo[4,5-b]pyridine with sulfur at 230–260° C. according to the methods described in Y. M. Yutilov, *Khim. Geterotsikl Doedin.* 6: 799–804 (1988). 6-Bromo-1H-imidazo[4,5-b]pyridine can be obtained from Sigma-Aldrich Chemical Company. Alternatively, 6-bromo-1H-imidazo[4,5-b]pyridine can be prepared by treating 2,3-diamino-5-bromopyridine with formic acid in polyphosphoric acid using methodology similar to that described by P. K. Dubey et al., *Indian J. Chem.* 16B(6):53 1–533 (1978). 2,3-Diamino-5-bromopyridine can be prepared in 97% yield by heating 2-amino-5-bromo-3-nitropyridine (commercially available from Aldrich Chemical Company and Lancaster Synthesis, Inc) with tin(II) chloride dihydrate in boiling ethanol according to the techniques described by S. X. Cai et al., *J. Med. Chem.*, 40(22): 3679–3686 (1997). Alternatively, 6-bromo-1H-imidazo[4,5-b]pyridine-2-thiol can be prepared by heating 2,3-diamino-5-bromopyridine with $K^{+-}SCSOEt$ in aqueous ethanol using methodology similar to that described by T. C. Kuhler et al., *J. Med Chem.* 38(25): 4906–4916 (1995). 2,3-Diamino-5-bromopyridine can be prepared from 2-amino-5-bromo-3-nitropyridine as described above.

In a related example, 6-bromo-2-phenylmethylthio-1H-imidazo[4,5-b]pyridine can be coupled via Heck reaction with the previously mentioned olefinic amine side chain, N-methyl-N-(tert-butoxycarbonyl)-4-penten-2-amine. The resulting Boc-protected intermediate can be subjected to treatment with a strong acid, such as trifluoroacetic acid to produce (4E)-N-methyl-5-(6-(2-phenylmethylthio-1H-imidazo[4,5-b]pyridin)yl)-4-penten-2-amine. The required bromo compound, 6-bromo-2-phenylmethylthio-1H-imidazo[4,5-b]pyridine can be prepared by alkylating the previously described 6-bromo-1H-imidazo[4,5-b]pyridine-2-thiol with benzyl bromide in the presence of potassium carbonate and N,N-dimethylformamide.

In another example, 6-bromooxazolo[4,5-b]pyridine, when submitted sequentially to palladium catalyzed coupling to N-methyl-N-(tert-butoxycarbonyl)-4-penten-2-amine and deprotection with trifluoroacetic acid, gives (4E)-N-methyl-5-(6-oxazolo[4,5-b]pyridinyl)-4-penten-2-amine. The requisite 6-bromooxazolo[4,5-b]pyridine can be produced from 2-amino-5-bromo-3-pyridinol by condensation with formic acid or a trialkyl orthoformate, using methodology similar to that of M-C. Viaud et al., *Heterocycles* 41: 2799–2809 (1995). The use of other carboxylic acids produces 2-substituted-6-bromooxazolo[4,5-b]pyridines, which are also substrates for the Heck reaction. The synthesis of 2-amino-5-bromo-3-pyridinol proceeds from furfurylamine (Aldrich Chemical Company). Thus, 5-bromo-3-pyridinol (produced from furfurylamine according to U.S. Pat. No. 4,192,946) can be chlorinated, using methods described by V. Koch et al., *Synthesis*, 499 (1990), to give 2-chloro-5-bromo-3-pyridinol, which in turn can be converted to 2-amino-5-bromo-3-pyridinol by treatment with ammonia.

5-Bromooxazolo[5,4-b]pyridine, isomeric by orientation of ring fusion to the previously described 6-bromooxazolo[4,5-b]pyridine, can also be used in the Heck coupling with N-methyl-N-(tert-butoxycarbonyl)-4-penten-2-amine. Subsequent removal of the tert-butoxycarbonyl protecting group provides (4E)-N-methyl-5-(5-oxazolo[5,4-b]pyridinyl)-4-penten-2-amine. The required 5-bromooxazolo[5,4-b]

pyridine is synthesized from 3-amino-5-bromo-2-pyridinol (3-amino-5-bromo-2-pyridone) by the condensation with formic acid (or a derivative thereof) as described above. 3-Amino-5-bromo-2-pyridinol can be made by bromination (using techniques described by T. Batkowski, *Rocz. Chem.* 41: 729–741 (1967)) and subsequent tin(II) chloride reduction (according to the method described by S. X. Cai et al., *J. Med. Chem.* 40(22): 3679–3686 (1997)) of commercially available 3-nitro-2-pyridinol (Aldrich Chemical Company).

Other polycyclic aromatic compounds of the present invention can be prepared by the Heck reaction. Thus both 5-bromofuro[2,3-b]pyridine and 5-bromo-1H-pyrrolo[2,3-b]pyridine can undergo palladium catalyzed coupling with the previously described olefinic amine side chain, N-methyl-N-(tert-butoxycarbonyl)-4-penten-2-amine, to give (4E)-N-methyl-N-(tert-butoxycarbonyl)-5-(5-furo[2,3-b]pyridinyl)-4-penten-2-amine and (4E)-N-methyl-N-(tert-butoxycarbonyl)-5-(5–1H-pyrrolo[2,3-b]pyridinyl)-4-penten-2-amine respectively. Subsequent removal of the tert-butoxycarbonyl group with trifluoroacetic acid will provide (4E)-N-methyl-5-(5-furo[2,3-b]pyridinyl)-4-penten-2-amine and (4E)-N-methyl-5-(5-1H-pyrrolo[2,3-b]pyridinyl)-4-penten-2-amine. The requisite 5-bromofuro[2,3-b]pyridine and 5-bromo-1H-pyrrolo[2,3-b]pyridine can be made from 2,3-dihydrofuro[2,3-b]pyridine and 2,3-dihydropyrrolo[2,3-b]pyridine respectively, by bromination (bromine and sodium bicarbonate in methanol) and dehydrogenation (2,3-dichloro-5,6-dicyano-1,4-benzoquinone), using chemistry described by E. C. Taylor et al., *Tetrahedron* 43: 5145–5158 (1987). 2,3-Dihydrofuro[2,3-b]pyridine and 2,3-dihydropyrrolo[2,3-b]pyridine are, in turn, made from 2-chloropyrimidine (Aldrich Chemical Company), as described by A. E. Frissen et al., *Tetrahedron* 45: 803–812 (1989), by nucleophilic displacement of the chloride (with the sodium salt of 3-butyn-1-ol or with 4-amino-1-butyne) and subsequent intramolecular Diels-Alder reaction. Using similar chemistry, 2,3-dihydrofuro[2,3-b]pyridine and 2,3-dihydropyrrolo[2,3-b]pyridine are also produced from 3-methylthio-1,2,4-triazene (E. C. Taylor et al., *Tetrahedron* 43: 5145–5158 (1987)), which in turn is made from glyoxal and S-methylthiosemicarbazide (W. Paudler et al., *J. Heterocyclic Chem.* 7: 767–771 (1970)).

Brominated dihydrofuropyridines, dihydropyrrolopyridines, and dihydropyranopyridines are also substrates for the palladium catalyzed coupling. For instance, both 5-bromo-2,3-dihydrofuro[2,3-b]pyridine and 5-bromo-2,3-dihydropyrrolo[2,3-b]pyridine (from bromination of 2,3-dihydrofuro[2,3-b]pyridine and 2,3-dihydropyrrolo[2,3-b]pyridine, as described above) can be coupled with the previously mentioned olefinic amine side chain in a Heck process. Subsequent deprotection gives the corresponding (4E)-N-methyl-5-(5-(2,3-dihydrofuro[2,3-b]pyidin)yl)-4-penten-2-amine and (4E)-N-methyl-5-(5-(2,3-dihydropyrrolo[2,3-b]pyridin)yl)-4-penten-2-amine. Similar treatment of 6-bromo-2,3-dihydrofuro[3,2-b]pyridine (isomeric at the ring fusion with the [2,3-b] system) will provide (4E)-N-methyl-5-(6-(2,3-dihydrofuro[3,2-b]pyridn)yl)-4-penten-2-amine. The requisite 6-bromo-2,3-dihydrofuro[3,2-b]pyridine can be made from 5-bromo-2-methyl-3-pyridinol by sequential treatment with two equivalents of lithium diisopropylamide (to generate the 2-methylenyl, 3-oxy dianion) and one equivalent of dibromomethane. Alternatively, using chemistry similar to that described by M. U. Koller et al., *Synth. Commun.* 25: 2963–74 (1995), the silyl-protected pyridinol (5-bromo-2-methyl-3-trimethylsilyloxypyridine) can be treated sequentially with one equivalent of lithium diisopropylamide and an alkyl or aryl aldehyde to produce a 2-(2-(1-alkyl- or 1-aryl-1-hydroxy)ethyl)-5-bromo-3-(trimethylsilyloxy)pyridine. Such materials can be converted, by methods (such as acid catalyzed cyclization or the Williamson synthesis) known to those skilled in the art, into the corresponding cyclic ethers (2-alkyl- or 2-aryl-6-bromo-2,3-dihydrofuro[3,2-b]pyridines. Similar chemistry, in which epoxides (instead of aldehydes) are used in reaction with the pyridylmethyl carbanion, leads to 2-alkyl- and 2-aryl-7-bromo-2,3-dihydropyrano[3,2-b]pyridines. These 2-substituted, brominated dihydrofuro- and dihydropyranopyridines are also substrates for the Heck reaction. For instance, 6-bromo-2,3-dihydro-2-phenylfuro[3,2-b]pyridine can be coupled, in a palladium catalyzed process, with N-methyl-N-(tert-butoxycarbonyl)-4-penten-2-amine, and the coupling product treated with trifluoroacetic acid (to remove the tert-butoxycarbonyl group), to give (4E)-N-methyl-5-(6-(2,3-dihydro-2-phenylfuro [3,2-b]pyridin)yl)-4-penten-2-amine.

The 5-bromo-2-methyl-3-pyridinol, required for the syntheses of the brominated dihydrofuro- and dihydropyranopyridines, is produced by standard transformations of commercially available materials. Thus, 2-methylnicotinic acid (Aldrich Chemical Company) can be converted, by sequential treatment with thionyl chloride, bromine, and ammonia (methodology described by C. V. Greco et al., *J. Heterocyclic Chem.* 7: 761–766 (1970)), into 5-bromo-2-methylnicotinamide. Hofmann rearrangement of 5-bromo-2-methylnicotinamide with hypochlorite will give 3-amino-5-bromo-2-methylpyridine, which can be converted to 5-bromo-2-methyl-3-pyridinol by diazotization with sodium nitrite in aqueous sulfuric acid. Alternatively, alanine ethyl ester (Aldrich Chemical Company) is converted (using ethyl formate) into its N-formyl derivative, which is then converted to 5-ethoxy-4-methyloxazole using phosphorous pentoxide (N. Takeo et al., Japan Patent No. 45,012,732). Diels-Alder reaction of 5-ethoxy-4-methyloxazole with acrylonitrile gives 5-hydroxy-6-methylnicotinonitrile (T. Yoshikawa et al., *Chem. Pharm. Bull.* 13: 873 (1965)), which is converted to 5-amino-2-methyl-3-pyridinol by hydration (nitrite→amide) and Hofmann rearrangement (Y. Morisawa et al., *Agr. Biol. Chem.* 39: 1275–1281 (1975)). The 5-amino-2-methyl-3-pyridinol can then be converted, by diazotization in the presence of cuprous bromide, to the desired 5-bromo-2-methyl-3-pyridinol.

Alternatively, the aryl substituted olefinic amine compounds of the present invention can be prepared by coupling an N-protected aminoaldehyde, such as 4-(N-methyl-N-(tert-butoxycarbonyl)amino)pentanal with an aryllithium. The required aldehyde can be prepared according to methodology described by Otsuka et al., *J. Am Chem. Soc.* 112: 838–845 (1990), starting from commercially available 1,5-dimethyl-2-pyrrolidinone (Aldrich Chemical Company). Thus, heating 1,5-dimethyl-2-pyrrolidinone with 6N hydrochloric acid forms 4-(methylamino)pentanoic acid, which can be readily esterified to ethyl 4-(methylamino) pentanoate. The latter compound can be treated with one equivalent of di-tert-butyl dicarbonate to give ethyl 4-(N-methyl-N-(tert-butoxycarbonyl)amino)pentanoate which is then reduced with DIBAL-H to give 4-(N-methyl-N-(tert-butoxycarbonyl)amino)pentanal. Reaction of this aldehyde with an aryllithium generates an alcohol, which can subsequently be converted to the N-protected olefinic amine by conversion of the alcohol to the alkyl halide (with, for instance, carbon tetrachloride and triphenylphosphine) and subsequent dehydrohalogenation (with 1,8-diazabicyclo[5.4.0]undec-7-ene). Removal of the tert-butoxycarbonyl protecting group, with trifluoroacetic acid, affords the desired (E)-5-aryl-4-penten-2-amine. Thus, 3-lithio-5-isopropoxypyridine (from 3-bromo-5-isopropoxypyridine and n-butyllithium) can be condensed with 4-(N-methyl-N-(tert-butoxycarbonyl)amino)pentanal to give 1-(3-(5-isopropoxypyridin)yl)-4-(N-methyl-N-(tert-butoxycarbonyl)amino)-1-pentanol, which can subsequently be converted into (4E)-N-methyl-5-(3-(5-isopropoxypyridin)yl)-4-penten-2-amine.

The R and S enantiomers of 1,5-dimethyl-2-pyrrolidinone can be made from commercially available (R)- and (S)-5-(hydroxymethyl)-2-pyrrolidinone (Aldrich Chemical Company). Thus, reaction of the enantiomerically pure hydroxymethylpyrrolidinone with carbon tetrabromide and triphenylphosphine in acetonitrile gives the corresponding 5-(bromomethyl)-2-pyrrolidinone (Pfaltz et al., *Helv. Chim. Acta* 79: 961 (1996)), which is reduced to the 5-methylpyrrolidinone by tri-n-butyltin hydride in toluene (Otsuka et al., *J. Amer. Chem. Soc.* 112: 838 (1990)). Subsequent methylation using sodium hydride and methyl iodide in tetrahydrofuran gives the enantiomerically pure 1,5-dimethyl-2-pyrrolidinone.

The methods by which enantiomerically pure 4-(N-methyl-N-(tert-butoxycarbonyl)amino)pentanal is synthesized can vary. Using methodology similar to that reported by Schessinger et al., *Tetrahedron Lett.* 28: 2083–2086 (1987), either N-methyl-L-alanine or N-methyl-D-alanine (available from Sigma) can be reacted sequentially with lithium aluminum hydride (to give the corresponding N-methylaminopropanols), di-tert-butyl dicarbonate (to protect the amino group), and p-toluenesulfonyl chloride (to esterify the alcohol). The resulting (S)- or (R)-1-p-toluenesulfonyloxy-N-methyl-N-(tert-butoxycarbonyl)-2-propanamine can be used to alkylate lithium acetylide to give the corresponding (S)- or (R)-N-methyl-N-(tert-butoxycarbonyl)-4-pentyn-2-amines. These, in turn, can be hydroborated and oxidized, by methods described by H. C. Brown et al., *J. Amer. Chem. Soc.* 97: 5249 (1975), to give (S)- or (R)-4-(N-methyl-N-(tert-butoxycarbonyl)amino) pentanal.

Fused ring heterocycles can also be lithiated and condensed with 4-(N-methyl-N-(tert-butoxycarbonyl)amino) pentanal. For example, 6-chloro-2-phenylfuro[3,2-b] pyridine can be treated sequentially with n-butyllithium and with 4-(N-methyl-N-(tert-butoxycarbonyl)amino)pentanal to give 1-(6-(2-phenylfuro [3,2-b]pyridin)yl)-4-(N-methyl-N-(tert-butoxycarbonyl)amino)-1-pentanol. Conversion of the alcohol to the alkyl halide, and subsequent dehydrohalogention and deprotection, gives (4E)-N-methyl-5-(6-(2-phenylfuro[3,2-b]pyridin)yl)-4-penten-2-amine. The requisite 6-chloro-2-phenylfuro[3,2-b]pyridine can be produced, using methodology similar to that described by A. Arcadi et al., *Synthesis*, 749 (1986), in which 5-chloro-2-iodo-3-pyridinol is reacted with phenylacetylene in the presence of palladium(II) acetate and cuprous iodide. In turn, the 5-chloro-2-iodo-3-pyridinol can be made by iodination of commercially available 5-chloro-3-pyridinol (Aldrich Chemical Company) using methods described by V. Koch et al., *Synthesis*, 497 (1990).

The present invention relates to a method for providing prevention of a condition or disorder to a subject susceptible to such a condition or disorder, and for providing treatment to a subject suffering therefrom. For example, the method comprises administering to a patient an amount of a compound effective for providing some degree of prevention of the progression of a CNS disorder (i.e., provide protective effects), amelioration of the symptoms of a CNS disorder, and amelioration of the recurrence of a CNS disorder. The method involves administering an effective amount of a compound selected from the general formulae which are set forth hereinbefore. The present invention relates to a pharmaceutical composition incorporating a compound selected from the general formulae which are set forth hereinbefore. Optically active compounds can be employed as racemic mixtures or as enantiomers. The compounds can be employed in a free base form or in a salt form (e.g., as pharmaceutically acceptable salts). Examples of suitable pharmaceutically acceptable salts include inorganic acid addition salts such as hydrochloride, hydrobromide, sulfate, phosphate, and nitrate; organic acid addition salts such as acetate, galactarate, propionate, succinate, lactate, glycolate, malate, tartrate, citrate, maleate, fumarate, methanesulfonate, p-toluenesulfonate, and ascorbate; salts with acidic amino acid such as aspartate and glutamate; alkali metal salts such as sodium salt and potassium salt; alkaline earth metal salts such as magnesium salt and calcium salt; ammonium salt; organic basic salts such as trimethylamine salt, triethylamine salt, pyridine salt, picoline salt, dicyclohexylamine salt, and N,N'-dibenzylethylenediamine salt; and salts with basic amino acid such as lysine salt and arginine salt. The salts may be in some cases hydrates or ethanol solvates. Representative salts are provided as described in U.S. Pat. No. 5,597,919 to Dull et al., U.S. Pat. No. 5,616,716 to Dull et al. and U.S. Pat. No. 5,663,356 to Ruecroft et al.

Compounds of the present invention are useful for treating those types of conditions and disorders for which other types of nicotinic compounds have been proposed as therapeutics. See, for example, Williams et al. *DN&P* 7(4):205–227 (1994), Arneric et al., *CNS Drug Rev.* 1(1):1–26 (1995), Arneric et al., *Exp. Opin. Invest. Drugs* 5(1):79–100 (1996), Bencherif et al., *JPET* 279:1413 (1996), Lippiello et al., *JPET* 279:1422 (1996), Damaj et al., *Neuroscience* (1997), Holladay et al., *J. Med. Chem* 40(28): 4169–4194 (1997), Bannon et al., *Science* 279: 77–80 (1998), PCT WO 94/08992, PCT WO 96/31475, and U.S. Pat. No. 5,583,140 to Bencherif et al., U.S. Pat. No. 5,597,919 to Dull et al., and U.S. Pat. No. 5,604,231 to Smith et al. Compounds of the present invention can be used as analgesics, to treat ulcerative colitis, and to treat convulsions such as those that are symptomatic of epilepsy. CNS disorders which can be treated in accordance with the present invention include presenile dementia (early onset Alzheimer's disease), senile dementia (dementia of the Alzheimer's type), Parkinsonism including Parkinson's disease, Huntington's chorea, tardive dyskinesia, hyperkinesia, mania, attention deficit disorder, anxiety, dyslexia, schizophrenia and Tourette's syndrome.

The pharmaceutical composition also can include various other components as additives or adjuncts. Exemplary pharmaceutically acceptable components or adjuncts which are employed in relevant circumstances include antioxidants, free radical scavenging agents, peptides, growth factors, antibiotics, bacteriostatic agents, immunosuppressives, anticoagulants, buffering agents, anti-inflammatory agents, anti-pyretics, time release binders, anaesthetics, steroids and corticosteroids. Such components can provide additional therapeutic benefit, act to affect the therapeutic action of the pharmaceutical composition, or act towards preventing any potential side effects which may be posed as a result of administration of the pharmaceutical composition. In certain circumstances, a compound of the present invention can be employed as part of a pharmaceutical composition with other compounds intended to prevent or treat a particular disorder.

The manner in which the compounds are administered can vary. The compounds can be administered by inhalation (e.g., in the form of an aerosol either nasally or using delivery articles of the type set forth in U.S. Pat. No. 4,922,901 to Brooks et al.); topically (e.g., in lotion form); orally (e.g., in liquid form within a solvent such as an aqueous or non-aqueous liquid, or within a solid carrier); intravenously (e.g., within a dextrose or saline solution); as an infusion or injection (e.g., as a suspension or as an emulsion in a pharmaceutically acceptable liquid or mixture of liquids); intrathecally; intracerebro ventricularly; or transdermally (e.g., using a transdermal patch). Although it is possible to administer the compounds in the form of a bulk active chemical, it is preferred to present each compound in the form of a pharmaceutical composition or formulation for efficient and effective administration. Exemplary methods for administering such compounds will be apparent to the skilled artisan. For example, the compounds can be administered in the form of a tablet, a hard gelatin capsule or as a time release capsule. As another example, the compounds can be delivered transdermally using the types of patch technologies available from Novartis and Alza Corporation. The administration of the pharmaceutical compositions of the present invention can be intermittent, or at a gradual, continuous, constant or controlled rate to a warm-blooded animal, (e.g., a mammal such as a mouse, rat, cat, rabbit, dog, pig, cow, or monkey); but advantageously is preferably administered to a human being. In addition, the time of day and the number of times per day that the pharmaceutical formulation is administered can vary. Administration preferably is such that the active ingredients of the pharmaceutical formulation interact with receptor sites within the body of the subject that affect the functioning of the CNS. More specifically, in treating a CNS disorder administration preferably is such so as to optimize the effect upon those relevant receptor subtypes which have an effect upon the functioning of the CNS, while minimizing the effects upon muscle-type receptor subtypes. Other suitable methods for administering the compounds of the present invention are described in U.S. Pat. No. 5,604,231 to Smith et al., the disclosure of which is incorporated herein by reference in its entirety.

The appropriate dose of the compound is that amount effective to prevent occurrence of the symptoms of the disorder or to treat some symptoms of the disorder from which the patient suffers. By "effective amount", "therapeutic amount" or "effective dose" is meant that amount sufficient to elicit the desired pharmacological or therapeutic effects, thus resulting in effective prevention or treatment of the disorder. Thus, when treating a CNS disorder, an effective amount of compound is an amount sufficient to pass across the blood-brain barrier of the subject, to bind to relevant receptor sites in the brain of the subject, and to activate relevant nicotinic receptor subtypes (e.g., provide neurotransmitter secretion, thus resulting in effective prevention or treatment of the disorder). Prevention of the disorder is manifested by delaying the onset of the symptoms of the disorder. Treatment of the disorder is manifested by a decrease in the symptoms associated with the disorder or an amelioration of the recurrence of the symptoms of the disorder.

The effective dose can vary, depending upon factors such as the condition of the patient, the severity of the symptoms of the disorder, and the manner in which the pharmaceutical composition is administered. For human patients, the effective dose of typical compounds generally requires administering the compound in an amount sufficient to activate relevant receptors to effect neurotransmitter (e.g., dopamine) release but the amount should be insufficient to induce effects on skeletal muscles and ganglia to any significant degree. The effective dose of compounds will of course differ from patient to patient but in general includes amounts starting where CNS effects or other desired therapeutic effects occur, but below the amount where muscular effects are observed.

Typically, the effective dose of compounds generally requires administering the compound in an amount of less than 5 mg/kg of patient weight. Often, the compounds of the present invention are administered in an amount from less than about 1 mg/kg patient weight, and usually less than about 100 ag/kg of patient weight, but frequently between about 10 ug to less than 100 u/kg of patient weight, and preferably between about 10 ug to about 50 ug/kg of patient weight. For preferred compounds of the present invention that do not induce effects on muscle type nicotinic receptors at low concentrations, the effective dose is less than 5 mg/kg of patient weight; and often such compounds are administered in an amount from 50 ug to less than 5 mg/kg of patient weight. The foregoing effective doses typically represent that amount administered as a single dose, or as one or more doses administered over a 24 hour period.

For human patients, the effective dose of typical compounds generally requires administering the compound in an amount of at least about 1, often at least about 10, and frequently at least about 25 ug/24 hr./patient. For human patients, the effective dose of typical compounds requires administering the compound which generally does not exceed about 500, often does not exceed about 400, and frequently does not exceed about 300 ug/24 hr./patient. In addition, administration of the effective dose is such that the concentration of the compound within the plasma of the patient normally does not exceed 500 ng/ml, and frequently does not exceed 100 ng/ml.

The compounds useful according to the method of the present invention have the ability to pass across the blood-brain barrier of the patient. As such, such compounds have the ability to enter the central nervous system of the patient. The log P values of typical compounds, which are useful in carrying out the present invention are generally greater than about 0, often are greater than about 0.5, and frequently are greater than about 1. The log P values of such typical compounds generally are less than about 3.5, often are less than about 3, and sometimes are less than about 2.5. Log P values provide a measure of the ability of a compound to pass across a diffusion barrier, such as a biological membrane. See, Hansch, et al., *J. Med. Chem.* 11:1 (1968).

The compounds useful according to the method of the present invention have the ability to bind to, and in most circumstances, cause activation of, nicotinic cholinergic receptors of the brain of the patient (e.g., such as those receptors that modulate dopamine release). As such, such compounds have the ability to express nicotinic pharmacology, and in particular, to act as nicotinic agonists. The receptor binding constants of typical compounds useful in carrying out the present invention generally exceed about 0.1 nM, often exceed about 1 nM, and frequently exceed about 10 nM. The receptor binding constants of such typical compounds generally are less than about 1 uM, often are less than about 100 nM, and frequently are less than about 50 nM. Receptor binding constants provide a measure of the ability of the compound to bind to half of the relevant receptor sites of certain brain cells of the patient. See, Cheng, et al., *Biochem. Pharmacol.* 22:3099 (1973).

The compounds useful according to the method of the present invention have the ability to demonstrate a nicotinic function by effectively eliciting ion flux through, and/or neurotransmitter secretion from, nerve ending preparations (e.g., thalamic or striatal synaptosomes). As such, such compounds have the ability to cause relevant neurons to become activated, and to release or secrete acetylcholine, dopamine, or other neurotransmitters. Generally, typical compounds useful in carrying out the present invention effectively provide for relevant receptor activation in amounts of at least about 30 percent, often at least about 50 percent, and frequently at least about 75 percent, of that maximally provided by (S)-(−)-nicotine. Generally, typical compounds useful in carrying out the present invention are more potent than (S)-(−)-nicotine in eliciting relevant receptor activation. Generally, typical compounds useful in carrying out the present invention effectively provide for the secretion of dopamine in amounts of at least about 50 percent, often at least about 75 percent, and frequently at least about 100 percent, of that maximally provided by (S)-(−)-nicotine. Certain compounds of the present invention can provide secretion of dopamine in an amount which can exceed that maximally provided by (S)-(−)-nicotine. Generally, typical compounds useful in carrying out the present invention are less potent than (S)-(−)-nicotine in eliciting neurotransmitter secretion, such as dopamine secretion.

The compounds of the present invention, when employed in effective amounts in accordance with the method of the present invention, lack the ability to elicit activation of nicotinic receptors of human muscle to any significant degree. In that regard, the compounds of the present invention demonstrate poor ability to cause isotopic rubidium ion flux through nicotinic receptors in cell preparations expressing muscle-type nicotinic acetylcholine receptors. Thus, such compounds exhibit receptor activation constants or EC50 values (i.e., which provide a measure of the concentration of compound needed to activate half of the relevant receptor sites of the skeletal muscle of a patient) which are extremely high (i.e., greater than about 100 uM). Generally, typical preferred compounds useful in carrying the present invention activate isotopic rubidium ion flux by less than 10 percent, often by less than 5 percent, of that maximally provided by S(−) nicotine.

The compounds of the present invention, when employed in effective amounts in accordance with the method of the present invention, are selective to certain relevant nicotinic receptors, but do not cause significant activation of receptors associated with undesirable side effects. By this is meant that a particular dose of compound resulting in prevention and/or treatment of a CNS disorder, is essentially ineffective in eliciting activation of certain ganglionic-type nicotinic receptors. This selectivity of the compounds of the present invention against those receptors responsible for cardiovascular side effects is demonstrated by a lack of the ability of those compounds to activate nicotinic function of adrenal chromaffin tissue. As such, such compounds have poor ability to cause isotopic rubidium ion flux through nicotinic receptors in cell preparations derived from the adrenal gland. Generally, typical preferred compounds useful in carrying out the present invention activate isotopic rubidium ion flux by less than 10 percent, often by less than 5 percent, of that maximally provided by S(−) nicotine.

Compounds of the present invention, when employed in effective amounts in accordance with the method of the present invention, are effective towards providing some degree of prevention of the progression of CNS disorders, amelioration of the symptoms of CNS disorders, and amelioration to some degree of the recurrence of CNS disorders. However, such effective amounts of those compounds are not sufficient to elicit any appreciable side effects, as is demonstrated by decreased effects on preparations believed to reflect effects on the cardiovascular system, or effects to skeletal muscle. As such, administration of compounds of the present invention provides a therapeutic window in which treatment of certain CNS disorders is provided, and side effects are avoided. That is, an effective dose of a compound of the present invention is sufficient to provide the desired effects upon the CNS, but is insufficient (i.e., is not at a high enough level) to provide undesirable side effects. Preferably, effective administration of a compound of the present invention resulting in treatment of CNS disorders occurs upon administration of less ⅓, frequently less than ⅕, and often less than 1/10, that amount sufficient to cause any side effects to a significant degree. amount sufficient to cause certain side effects to any significant degree.

The pharmaceutical compositions of the present invention can be employed to prevent or treat certain other conditions, diseases and disorders. Exemplary of such diseases and disorders include inflammatory bowel disease, acute cholangitis, aphteous stomatitis, arthritis (e.g., rheumatoid arthritis and osteoarthritis), neurodegenerative diseases, cachexia secondary to infection (e.g., as occurs in AIDS, AIDS related complex and neoplasia), as well as those indications set forth in PCT WO 98/25619. The pharmaceutical compositions of the present invention can be employed in order to ameliorate may of the symptoms associated with those conditions, diseases and disorders. Thus, pharmaceutical compositions of the present invention can be used in treating genetic diseases and disorders, in treating autoimmune disorders such as lupus, as anti-infectious agents (e.g, for treating bacterial, fungal and viral infections, as well as the effects of other types of toxins such as sepsis), as anti-inflammatory agents (e.g., for treating acute cholangitis, aphteous stomatitis, asthma, and ulcerative colitis), and as inhibitors of cytokines release (e.g., as is desirable in the treatment of cachexia, inflammation, neurodegenerative diseases, viral infection, and neoplasia), The compounds of the present invention can also be used as adjunct therapy in combination with existing therapies in the management of the aforementioned types of diseases and disorders. In such situations, administration preferably is such that the active ingredients of the pharmaceutical formulation act to optimize effects upon abnormal cytokine production, while minimizing effects upon receptor subtypes such as those that are associated with muscle and ganglia. Administration preferably is such that active ingredients interact with regions where cytokine production is affected or occurs. For the treatment of such conditions or disorders, compounds of the present invention are very potent (i.e., affect cytokine production and/or secretion at very low concentrations), and are very efficacious (i.e., significantly inhibit cytokine production and/or secretion to a relatively high degree).

Effective doses for such applications are most preferably at very low concentrations, where maximal effects are observed to occur. Concentrations, determined as the amount of compound per volume of relevant tissue, typically provide a measure of the degree to which that compound affects cytokine production. Typically, the effective dose of compounds generally requires administering the compound in an amount of much less than 100 ug/kg of patient weight, and even less than 10 ug/kg of patient weight. The foregoing effective doses typically represent that amount administered as a single dose, or as one or more doses administered over a 24 hour period.

For human patients, the effective dose of typical compounds generally requires administering the compound in an amount of at least about 1, often at least about 10, and frequently at least about 25 ug/24 hr./patient. For human patients, the effective dose of typical compounds requires administering the compound which generally does not exceed about 1, often does not exceed about 0.75, often does not exceed about 0.5, frequently does not exceed about 0.25 mg/24 hr./patient. In addition, administration of the effective dose is such that the concentration of the compound within the plasma of the patient normally does not exceed 500 pg/ml, often does not exceed 300 pg/ml, and frequently does not exceed 100 pg/ml. When employed in such a manner, compounds of the present invention are dose dependent, and as such, cause inhibition of cytokine production and/or secretion when employed at low concentrations but do not exhibit those inhibiting effects at higher concentrations. Compounds of the present invention exhibit inhibitory effects upon cytokine production and/or secretion when employed in amounts less than those amounts necessary to elicit activation of relevant nicotinic receptor subtypes to any significant degree.

The following examples are provided to illustrate the present invention, and should not be construed as limiting thereof. In these examples, all parts and percentages are by weight, unless otherwise noted. Reaction yields are reported in mole percentages. Several commercially available starting materials are used throughout the following examples. 3-Bromopyridine, 2-amino-5-bromopyrimidine, 2-amino-5-bromo-3-nitropyridine, furfurylamine, 4-bromo-1-butene and 4-penten-2-ol were obtained from Aldrich Chemical Company. (R)-(+)-propylene oxide was obtained from Fluka Chemical Company. 5-Bromonicotinic acid was obtained form Acros Organics or Aldrich Chemical Company. 3,5-Dibromopyridine was obtained form Lancaster Synthesis, Inc. or Aldrich Chemical Company. 3-Chloro-5-trifluoromethylpyridine was obtained form Strem Chemicals, Inc. Column chromatography was done using either Merck silica gel 60 (70–230 mesh) or aluminum oxide (activated, neutral, Brockmann I, standard grade, ~150 mesh). to Pressure reactions were done in a heavy wall glass pressure tube (185 mL capacity), with Ace-Thread, and plunger valve available from Ace Glass Inc. Reaction mixtures were typically heated using a high-temperature silicon oil bath, and temperatures refer to those of the oil bath. The following abbreviations are used in the following examples: $CHCl_3$ for chloroform, $CH_2Cl_2$ for dichloromethane, $CH_3OH$ for methanol, DMF for N,N-dimethylformamide, and EtOAc for ethyl acetate, THF for tetrahydrofuran, and $Et_3N$ for triethylamine.

EXAMPLES

Assays
Determination of Binding to Relevant Receptor Sites

Binding of the compounds to relevant receptor sites was determined in accordance with the techniques described in U.S. Pat. No. 5,597,919 to Dull et al. Inhibition constants (Ki values), reported in nM, were calculated from the $IC_{50}$ values using the method of Cheng et al., *Biochem, Pharmacol.* 22:3099 (1973).

Determination of Dopamine Release

Dopamine release was measured using the techniques described in U.S. Pat. No. 5,597,919 to Dull et al. Release is expressed as a percentage of release obtained with a concentration of (S)-(−)-nicotine resulting in maximal effects. Reported $EC_{50}$ values are expressed in nM, and $E_{max}$ values represent the amount released relative to (S)-(−)-nicotine on a percentage basis.

Neurotransmitter Release From Brain Synaptosomes

Neurotransmitter release was measured using techniques similar to those previously published (Bencherif M, et al . . . *JPET* 279: 1413–1421, 1996).

Rat brain synaptosomes were prepared as follows: Female Sprague Dawley rats (100–200 g) were killed by decapitation after anesthesia with 70% $CO_2$. Brains are dissected, and hippocampus, striatum, and thalamus isolated, and homogenized in 0.32 M sucrose containing 5 mM HEPES pH 7.4 using a glass/glass homogenizer. The tissue was then centrifuged for 1000×g for 10 minutes and the pellet discarded. The supernatant was centrifuged at 12000×g for 20 minutes. The resultant pellet was re-suspended in perfusion buffer (128 mM NaCl, 1.2 mM $KH_2PO_4$, 2.4 mM KCl, 3.2 mM $CaCl_2$, 1.2 mM $MgSO_4$, 25 mM HEPES, 1 mM Ascorbic acid, 0.01 mM pargyline HCl and 10 mM glucose pH 7.4) and centrifuged for 15 minutes at 25000×g. The final pellet was resuspended in perfusion buffer and placed in a water bath (37° C.) for 10 minutes. Radiolabeled neurotransmitter is added (30 µL $^3$H DA, 20 µL $^3$H NE, 10 µL $^3$H glutamate) to achieve a final concentration of 100 nM, vortexed and placed in a water bath for additional 10 minutes. Tissue-loaded filters is placed onto 11-mm diameter Gelman A/E filters on an open-air support. After a 10-minute wash period, fractions are collected to establish the basal release and agonist applied in the perfusion stream. Further fractions were collected after agonist application to re-establish the baseline. The perfusate was collected directly into scintillation vials and released radioactivity was quantified using conventional liquid scintillation techniques. Release of neurotransmitter was determined in the presence of 10µM of various ligands and was expressed as a percentage of release obtained with a concentration of 10 µM (S)-(−)-nicotine or 300 µM TMA resulting in maximal effects.

Determination of Rubidium Ion Release

Rubidium release was measured using the techniques described in Bencherif et al., *JPET*, 279: 1413–1421 (1996). Reported $EC_{50}$ values are expressed in nM, and Ema, values represent the amount of rubidium ion released relative to 300 uM tetramethylammonium ion, on a percentage basis.

Determination of Interaction with Muscle Receptors

The determination of the interaction of the compounds with muscle receptors was carried out in accordance with the techniques described in U.S. Pat. No. 5,597,919 to Dull et al. The maximal activation for individual compounds ($E_{max}$) was determined as a percentage of the maximal activation induced by (S)-(−)-nicotine. Reported $E_{max}$ values represent the amount released relative to (S)-(−)-nicotine on a percentage basis.

Determination of Interaction with Ganglion Receptors

The determination of the interaction of the compounds with ganglionic receptors was carried out in accordance with the techniques described in U.S. Pat. No. 5,597,919 to Dull et al. The maximal activation for individual compounds ($E_{max}$) was determined as a percentage of the maximal activation induced by (S)-(−)-nicotine. Reported $E_{max}$ values represent the amount released relative to (S)-(−)-nicotine on a percentage basis.

Example 1

Sample No. 1 is (3E)-N-methyl-4-[3-(5-nitro-6-aminopyridin)yl]-3-buten-1-amine, which was prepared in accordance with the following techniques:

N-Methyl-3-buten-1-amine

Under a nitrogen atmosphere, anhydrous DMF (40 mL) was added via syringe to methylamine (40 mL, 43.2 g, 1.4 mol, condensed from the gas phase) at −78° C. Anhydrous potassium carbonate (19.36 g, 140 mmol) was added to the stirring solution, followed by 4-bromo-1-butene (18.9 g, 140 mmol). The resulting mixture was allowed to slowly warm to room temperature overnight. The mixture was poured into water (150 mL) and extracted with ether (8×50 mL). The combined ether extracts were dried ($Na_2SO_4$), filtered, and distilled at atmospheric pressure to give 6.86 g (57.6%) of a colorless oil, bp 80–82° C. (lit. bp 87° C. at 760 mm Hg as reported by G. Courtois et al. *Bull. Soc. Chim. Fr.* (3): 449–453 (1986)).

N-Methyl-N-(3-buten-1-yl)benzamide

Under a nitrogen atmosphere, a solution of N-methyl-3-buten-1-amine (6.86 g, 80.6 mmol) in dichloromethane (100 mL) was cooled to 0° C., and triethylamine (17.93 g, 177.2 mmol) and 4-(N,N-dimethylamino)pyridine (207 mg) were added. A solution of benzoyl chloride (11.89 g, 84.6 mmol) in dichloromethane (60 mL) was added drop-wise via addition funnel over 1 h at 0–5° C. The resulting turbid mixture was stirred 3h at 0° C. The mixture was then washed in succession with 1M HCl solution (3×75 mL), 5% $NaHCO_3$ solution (3×100 mL), and water (100 mL). The organic phase was dried ($Na_2SO_4$), filtered, and concentrated on a rotary evaporator to a yellow oil (12.66 g). Vacuum distillation using a 6 in. Vigreaux column and a short path distillation apparatus afforded 8.58 g (56.3%) of a colorless oil, bp 100–103° C. at 0.1 mm Hg.

(3E)-N-Methyl-N-benzoyl-4-[3-(5-nitro-6-aminopyridin)yl]-3-buten-1-amine

Under a nitrogen atmosphere, a mixture of N-methyl-N-(3-buten-1-yl)benzamide (2.25 g, 11.9 mmol), 2-amino-5-bromo-3-nitropyridine (2.67 g, 11.9 mmol) (Aldrich Chemical Company), palladium(II) acetate (27.2 mg, 0.12 mmol), tri-o-tolylphosphine (74.6 mg, 0.24 mmol), and triethylamine (2.41 g, 24.0 mmol) was stirred and heated under reflux at 90–95° C. (oil bath temperature) for 20 h. More triethylamine (2.18 g, 21.5 mmol), palladium(II) acetate (27.2 mg, 11.9 mmol), tri-o-tolylphosphine (149.2 mg, 0.49 mmol), and acetonitrile (6.0 mL) were added, and the mixture was stirred and heated at 90–100° C. (oil bath temperature) for 120 h. TLC analysis ($CHCl_3$—$CH_3OH$, 98:2, v/v) of the mixture indicated an incomplete reaction, therefore more palladium(II) acetate (54.4 mg, 0.24 mmol), tri-o-tolylphosphine (295.0 mg, 0.97 mmol), and triethylamine (2.18 g, 21.5 mmol) were added. Reflux was continued for an additional 192 h at 110–115° C. (oil bath temperature). The resulting dark brown mixture of solids was cooled slightly and added to water (125 mL) and dichloromethane (150 mL), producing an emulsion. The aqueous layer was separated and extracted with dichloromethane (25 mL). The combined dichloromethane extracts were filtered, and the filtrate was washed with water (75 mL). The dark-brown dichloromethane layer was separated, dried ($Na_2SO_4$), filtered, and concentrated by rotary evaporation. The resulting product was dried in a vacuum oven at 30° C. for 16 h to give 3.85 g of a brown solid. The solid was dissolved in dichloromethane (100 mL) and washed with 1 M HCl solution (100 mL, 50 mL). The brown dichloromethane layer was separated and concentrated by rotary evaporation to a dark-brown, oily solid. 2-Propanol was added and the solution was concentrated by rotary evaporation. The resulting dark-brown residue was dried in a vacuum oven at 40° C. for 16 h to give 3.71 g of a brown solid. This solid was purified by column chromatography on silica gel (218.2 g) eluting with $CHCl_3$—$CH_3OH$ (98:2, v/v). Selected fractions, based upon TLC analysis, were combined to afford 2.00 g (51.7%) of a reddish orange powder. An analytical sample was prepared by the successive recrystallization of 1.28 g of material from the following solvents: benzene-petroleum ether (1:1, v/v), benzene, including a Darco® G-60 charcoal (0.10 g) and Hyflo Super Cel (0.10 g) treatment, and finally benzene (twice). The recrystallized product was air dried and further dried in a vacuum oven at 50° C. for 5 h to give 0.77 g of an orange powder, mp 162.5–164° C.

(3E)-N-Methyl-4-[3-(5-nitro-6-aminopyridin)yl]-3-buten-1-amine

Under a nitrogen atmosphere, a solution of (3E)-N-methyl-N-benzoyl-4-[3-(5-nitro-6-animopyridin)yl]-3-buten-1-amine (130.0 mg, 0.40 mmol) in 6 M HCl solution (20 mL) was stirred and heated under reflux at 145–150° C. (oil bath temperature) for 16 h. The resulting light yellow solution was allowed to cool to room temperature and was further cooled to 0° C. A 20% NaOH solution (30 mL) was added drop-wise with stirring to pH 12. The solution was extracted with dichloromethane (100 mL) which produced an emulsion. The biphasic mixture was filtered through a Buchner funnel, precoated with Hyflo Super Cel filter aid, washing the filter cake with dichloromethane (2×25 mL). The yellow dichloromethane layer was separated; the aqueous phase was extracted with dichloromethane (3×25 mL). The combined dichloromethane extracts were dried ($Na_2SO_4$), filtered, and concentrated by rotary evaporation to a yellow powder (86.6 mg). The crude product was purified by column chromatography on silica gel (8.1 g) eluting with THF-$CH_3OH$-conc. $NH_4OH$ (22:10:1, v/v/v). Based upon TLC analysis, selected fractions containing the product were combined and concentrated by rotary evaporation. The resulting solid was dissolved in dichloromethane, dried ($Na_2SO_4$), filtered, and concentrated by rotary evaporation. Further drying in a vacuum oven at 30° C. for 16 h gave 59.1 mg (66.7%) of a dark-orange powder, mp 118–121° C.

Sample No. 1 exhibits a Ki of 3 nM. The low binding constant indicates that the compound exhibits good high affinity binding to certain CNS nicotinic receptors. Sample No. 1 exhibits an $E_{max}$ value of 0% for dopamine release, indicating that the compound is selective in eliciting neurotransmitter release. The sample exhibits an $EC_{50}$ value of 26,000 nM and an $E_{max}$ value of 22% in the rubidium ion flux assay. The sample exhibits a neurotransmitter release $E_{max}$ value of 33%.

Sample No. 1 exhibits an $E_{max}$ of 10% (at a concentration of 100 uM) at muscle-type receptors, indicating that the compound does not significantly induce activation of muscle-type receptors. The sample exhibits an $E_{max}$ of 11% (at a concentration of 100 uM) at ganglionic-type receptors. The compound has the capability to bind to human CNS receptors without activating muscle-type and ganglionic-type nicotinic acetylcholine receptors to any significant degree. Thus, there is provided a therapeutic window for utilization in the treatment of CNS disorders. The compound begins to cause muscle effects and ganglion effects only when employed in amounts greater than those required to bind to certain CNS receptors, thus indicating a lack of undesirable side effects in subjects receiving administration of this compound.

Example 2

Sample No. 2 is (3E)-N-methyl-N-[3-(5-(N-benzylcarboxamido)pyridin)yl]-3-buten-1-amine, which was prepared in accordance with the following techniques:

N-Methyl-3-buten-1-amine

Under a nitrogen atmosphere, anhydrous DMF (40 mL) was added via syringe to methylamine (40 mL, 43.2 g, 1.4 mol, condensed from the gas phase) at −78° C. Anhydrous potassium carbonate (19.36 g, 140 mmol) was added to the stirring solution, followed by 4-bromo-1-butene (18.9 g, 140 mmol). The resulting mixture was allowed to slowly warm to room temperature overnight. The mixture was poured into water (150 mL) and extracted with ether (8×50 mL). The combined ether extracts were dried ($Na_2SO_4$), filtered, and distilled at atmospheric pressure to give 6.86 g (57.6%) of a colorless oil, bp 80–82° C. (lit. bp 87° C. at 760 mm Hg as reported by G. Courtois et al. *Bull. Soc. Chim. Fr.* (3): 449–453 (1986)).

N-Methyl-N-(tert-butoxycarbonyl)-3-buten-1-amine

Under a nitrogen atmosphere, a stirring, ice-cold (2° C.) solution of N-methyl-3-buten-1-amine (4.78 g, 56.2 mmol) in dry THF (20 mL, freshly distilled from sodium and benzophenone) was treated in portions with di-tert-butyl dicarbonate (12.26 g, 56.2 mmol) over 10 min., allowing the carbon dioxide evolution to subside between additions. The resulting colorless solution was allowed to warm to ambient temperature. The THF was removed by rotary evaporation, and the resulting light-yellow liquid was vacuum distilled using a 6 in. Vigreaux column and a short-path distillation apparatus. The fraction with bp 70° C. at 3.5 mm Hg was collected to give 4.19 g (40.2%) of a colorless oil.

5-Bromo-3-N-benzylnicotinamide

Under anhydrous conditions, thionyl chloride (4.12 g, 34.65 mmol) was added drop-wise via addition funnel to a cold (0° C.), stirring mixture of 5-bromonictinic acid (7.00 g, 34.65 mmol) (Acros Organics), pyridine (5.48 g, 69.28 mmol), and toluene (6 mL). The stirring mixture was heated to 105° C. (oil bath temperature), held at this temperature for 1 h, and then cooled to 70–75° C. A solution of benzylamine (3.71 g, 34.65 mmol) in toluene (10 mL) was added drop-wise over 5 min. at 70–75° C. via addition funnel, followed by the addition of more pyridine (9.14 g, 116.0 mmol). The dark-brown solution was heated at 90–95° C. (oil bath temperature) for 3 h and allowed to cool to ambient temperature. The reaction mixture was poured into 1 M HCl solution (150 mL), producing a biphasic mixture with solids present. The mixture was gently warmed and filtered to collect the solids. The product was vacuum dried at 45° C. for 15 h to give 6.90 g of cream-colored solids. The crude product was recrystallized from a small volume of absolute ethanol. The recrystallized material was filtered, washed with cold ethanol (2×20 mL), vacuum dried at 45° C. for 15 h to give 4.26 g of a light-beige, slightly pink, crystalline powder, mp 118–120° C. More product was obtained from the HCl-toluene filtrate: The toluene phase was separated and extracted with 1 M HCl solution (2×50 mL). The combined HCl extracts were cooled to 0° C., basified with 18% $Na_2CO_3$ solution to pH 9, extracted with toluene (50 mL), and extracted with $CH_2Cl_2$ (4×50 mL). The combined peach-colored toluene-$CH_2Cl_2$ extracts were dried ($Na_2SO_4$), filtered, concentrated on a rotary evaporator, and further vacuum dried at 45° C. for 15 h. The resulting reddish beige solids were recrystallized from a minimum amount (~5 mL) of absolute ethanol. The recrystallized second batch was filtered, washed with cold ethanol (2×10 mL), and vacuum dried at 45° C. for 3 h to give 2.09 g of a light-beige, slightly pink, crystalline powder, mp 118–120° C., bringing the total yield to 6.35 g (62.9%).

(3E)-N-Methyl-4-(tert-butoxycarbonyl)-4[3-(5-(N-benzylcarboxamido)pyridin)yl]-3-buten-1-amine Under a nitrogen atmosphere, a mixture of 5-bromo-3-N-benzylnicotinamide (2.50 g, 8.59 mmol), N-methyl-N-(tert-butoxycarbonyl)-3-buten-1-amine (1.59 g, 8.59 mmol), palladium(II) acetate (21.2 mg, 0.09 mmol), tri-o-tolylphosphine (115.0 mg, 0.38 mmol), triethylamine (2.39 g, 23.66 mmol) and anhydrous acetonitrile (6.6 mL) was stirred and heated under reflux at 95–100° C. (oil bath temperature) for 24 h, followed by further heating at 85–90° C. (oil bath temperature) for 60 h. The dark-brown mixture was allowed to cool to ambient temperature, diluted with water (20 mL) and $CH_2Cl_2$ (20 mL). The light-brown $CH_2Cl_2$ layer was separated, and the aqueous layer was extracted with $CH_2Cl_2$ (2×20 mL). The combined $CH_2Cl_2$ extracts were washed with water (10 mL), dried ($Na_2SO_4$), filtered, concentrated by rotary evaporation, and further vacuum dried for 3 h at 0.6 mm Hg to give 3.41 g of a brown oil. The crude product was purified by column chromatography on silica gel (150 g), eluting with 50–100% (v/v) ethyl acetate in hexane. Selected fractions containing the product ($R_f$ 0.31 in EtOAc-hexane (3:1, v/v)) were combined, concentrated by rotary evaporation, and vacuum dried to give 2.17 g (63.9%) of a light-yellow oil.

(3E)-N-Methyl-N-[3-(5-(N-benzylcarboxamido)pyridin)yl]-3-buten-1-amine

Under a nitrogen atmosphere, a solution of (3E)-N-methyl-N-(tert-butoxycarbonyl)-4-[3-(5-(N-benzylcarboxamido)pyridin)yl]-3-buten-1-amine (1.27 g, 3.21 mmol), anisole (1.74 g, 16.06 mmol), and $CHCl_3$ (12 mL) was treated with trifluoroacetic acid (14.80 g, 129.8 mmol). The resulting brown solution was stirred for 1 h and concentrated on a rotary evaporator, followed by further drying under high vacuum. The residue was basified with 20% NaOH solution (5 mL) to pH 12, saturated NaCl solution (3 mL) was added, and the mixture was extracted with $CHCl_3$ (4×10 mL). The combined $CHCl_3$ extracts were washed with saturated NaCl solution (10 mL), dried ($Na_2SO_4$), filtered, concentrated by rotary evaporation, followed by further drying under high vacuum to give 0.98 g of a foamy, brown residue. The crude product was purified by column chromatography on silica gel (45 g), eluting with $CH_3OH$-$Et_3N$ (97:3, v/v). Selected fractions containing the product ($R_f$ 0.24) were combined and concentrated on a rotary evaporator to a yellow residue that was dissolved in $CHCl_3$ (5 mL). The $CHCl_3$ solution was dried ($Na_2SO_4$), filtered, concentrated by rotary evaporation, and dried under high vacuum to give 30.1 mg (3.2%) of a light-yellow oil.

Sample No. 2 exhibits a Ki of 192 nM, indicating that the compound exhibits binding to certain CNS nicotinic receptors. Sample No. 2 exhibits an $EC_{50}$ value of 100,000 nM and an $E_{max}$ value of 12% for dopamine release.

Sample No. 1 exhibits an $E_{max}$ of 11% (at a concentration of 100 uM) at muscle-type receptors, indicating that the compound does not significantly induce activation of muscle-type receptors. The sample exhibits an $E_{max}$ of 16% (at a concentration of 100 uM) at ganglionic-type receptors. The compound has the capability to bind to human CNS receptors without activating muscle-type and ganglionic-type nicotinic acetylcholine receptors to any significant degree.

Example 3

Sample No. 3 is (4E)-N-Methyl-5-[5-(2-aminopyrimidin)yl]-4-penten-2-amine Hemigalactarate, which was prepared in accordance with the following techniques:

4-Penten-2-ol p-Toluenesulfonate

Under a nitrogen atmosphere, tosyl chloride (16.92 g, 88.75 mmol) was added to a cold (2° C.), stirring solution of 4-penten-2-ol (7.28 g, 84.52 mmol) in pyridine (60 mL). The solution was stirred at 2–5° C. for 2 h and allowed to warm to ambient temperature over several hours. The mixture, containing white solids was poured into cold 3 M HCl solution (250 mL) and extracted with $CHCl_3$ (4×75 mL). The combined $CHCl_3$ extracts were washed with 3 M HCl solution (4×100 mL), saturated NaCl solution (2×50 mL), dried ($Na_2SO_4$), filtered, concentrated on a rotary evaporator and further dried under high vacuum to afford 17.38 g (85.6%) of a light-amber oil.

N-Methyl-4-penten-2-amine

A 185 mL thick-walled glass pressure tube was charged with 4-penten-2-ol p-toluenesulfonate (17.30 g, 71.99 mmol) followed by a 40% solution of aqueous methylamine (111.85 g, 1.44 mol). The tube was sealed and the mixture was stirred and heated at 122° C. (oil bath temperature) for 16 h. The solution was cooled to ambient temperature and further cooled to 0–5° C. The light-yellow solution was saturated with NaCl and extracted with diethyl ether (6×40 mL, inhibitor-free). The combined ether extracts (light-yellow) were dried ($Na_2SO_4$) and filtered. The ether was removed by distillation at atmospheric pressure using a 6-inch Vigreaux column and a short-path distillation apparatus. The residual light-yellow oil was distilled at atmospheric pressure collecting 2.59 g (36.3%) of a colorless oil, bp 75–105° C.

N-Methyl-N-(tert-butoxycarbonyl)-4-penten-2-amine

Di-tert-butyl dicarbonate (6.84 g, 31.35 mmol) was quickly added in several portions to a cold (0–5° C.), stirring solution of N-methyl-4-penten-2-amine (2.55 g, 25.68 mmol) in THF (25 mL, freshly distilled from sodium and benzophenone). The resulting light-yellow solution was stirred and allowed to warm to ambient temperature over several hours. The solution was concentrated on a rotary evaporator. The resulting oil was vacuum distilled using a short-path distillation apparatus, collecting 4.61 g (90.0%) of an almost colorless oil, bp 85–86° C. at 5.5 mm Hg.

(4E)-N-Methyl-N-(tert-butoxycarbonyl)-5-[5-(2-aminopyrimidin)yl]-4-penten-2-amine A 185 mL thick-walled glass pressure tube was charged with 2-amino-5-bromopyrimidine (1.222 g, 7.025 mmol), palladium(II) acetate (15.77 mg, 0.070 mmol), tri-o-tolylphosphine (85.53 mg, 0.281 mmol), N-methyl-N-(tert-butoxycarbonyl)-4-penten-2-amine (1.400 g, 7.025 mmol), triethylamine (2.5 mL, 1.815 g, 17.937 mmol) and acetonitrile (5 mL). The tube was flushed with nitrogen, sealed and heated at 114° C. (oil bath temperature) for 17 h. The mixture was cooled and additional palladium(II) acetate (15.77 mg, 0.070 mmol), tri-o-tolylphosphine (85.53 mg, 0.281 mmol), triethylamine (2.5 mL) and acetonitrile (5 mL) were added. The tube was sealed and the mixture was further heated for 29 h at 115° C. The mixture was allowed to cool to ambient temperature and solidified as a dark-brown, crystalline solid. The solids were dissolved in a mixture of water (25 mL) and $CH_2Cl_2$ (25 mL). The aqueous phase was separated and extracted with $CH_2Cl_2$ (2×25 mL). The combined dark-brown $CH_2Cl_2$ extracts were washed with saturated NaCl solution (25 mL), dried ($Na_2SO_4$), filtered, concentrated by rotary evaporation and briefly dried under high vacuum to give a dark-brown, oily semi-solid (2.25 g). The crude product was purified by column chromatography on silica gel (125 g), eluting with $CHCl_3$—$CH_3OH$ (95:5, v/v). Selected fractions containing the product ($R_f$ 0.24) were combined and concentrated to give 1.46 g of a light-yellow oil. The product was re-chromatographed on silica gel (100 g), eluting with EtOAc-hexane (9:1, v/v). Selected fractions containing the product ($R_f$ 0.17) were combined and concentrated to give 0.59 g of a light-yellow oil. Impure fractions were concentrated to an oil that was re-chromatographed on silica gel (85 g), eluting with EtOAc-hexane (9:1, v/v). Pure fractions were combined and concentrated to give an additional 0.21 g of a light-yellow oil, bringing the total yield to 0.80 g (39.0%). Upon standing at ambient temperature, the oil solidified as a waxy, off-white glass, mp 84–92° C.

(4E)-N-Methyl-5-[5-(2-aminopyrimidin)yl]-4-penten-2-amine

Under a nitrogen atmosphere, a solution of (4E)-N-methyl-N-(tert-butoxycarbonyl)-5-[5-(2-aminopyrimidin)yl]-4-penten-2-amine (0.78 g, 2.668 mmol) in $CHCl_3$ (55 mL) was treated drop-wise at ambient temperature with lo iodotrimethylsilane (0.83 mL, 1.174 g, 5.869 mmol). The turbid, orange-brown solution was allowed to stir for 30 min. The solution was treated with methanol (55 mL), and the resulting dark-brown solution was stirred for 1 h at ambient temperature. The solution was concentrated by rotary evaporation to a brown, foamy residue. After cooling to 0° C., the residue was basified with 10% NaOH solution (15 mL), diluted with saturated NaCl solution (10 mL) and extracted with $CHCl_3$ (10×10 mL). The combined $CHCl_3$ extracts (yellow) were dried ($Na_2SO_4$), filtered, concentrated by rotary evaporation and briefly dried under high vacuum to give a brown oil (0.57 g). The crude product was purified by column chromatography on silica gel (65 g), eluting with $CH_3OH$—$NH_4OH$ (20:1, v/v). Fractions containing the product ($R_f$ 0.29) were combined and concentrated to give 0.04 g of a tan semi-solid. Impure fractions were combined and concentrated to a residue that was re-chromatographed on silica gel (65 g) in the same manner to yield an additional 0.09 g of a tan semi-solid. Impure fractions were combined and concentrated to a yellow oil that was re-chromatographed on silica gel (65 g), eluting with $CH_3OH$—$NH_4OH$ (10:1, v/v). Fractions containing the product ($R_f$ 0.48) were combined and concentrated to give an additional 0.07 g of a tan semi-solid. All of the purified material was dissolved in $CHCl_3$. The $CHCl_3$ solution was dried ($Na_2SO_4$), filtered and concentrated to a yellow oil that crystallized as oily, light-yellow crystals (0.215 g, 41.9%).

(4E)-N-Methyl-5[5-(2-aminopyrimidin)yl]-4-penten-2-amine Hemigalactarate

To a solution of (4E)-N-methyl-5-[5-(2-aminopyrimidin)yl]-4-penten-2-amine (209.7 mg, 1.091 mmol) in ethanol (3 mL) was added galactaric acid (114.6 mg, 0.545 mmol). Water (0.8 mL) was added drop-wise, while warming the solution to near reflux. To remove some white, insoluble crystals, the warm solution was filtered through a glass wool plug, washing the filter plug with a warm solution of ethanol-water (4:1, v/v) (2×1 mL). The filtrate was diluted with ethanol (5 mL). The mixture was allowed to cool to ambient temperature and was further cooled at 5° C. No solids precipitated. Consequently, the solution was concentrated by rotary evaporation, and the residue was further dried under high vacuum producing a yellow, crispy solid. The material was recrystallized from hot 2-propanol (~10 mL)—water (1.3 mL) producing a brown oil, containing a few solids. The mixture was cooled at 5° C. for 16 h. The resulting solids were filtered and washed with cold 2-propanol (4×2 mL). The light-beige solids were crushed and slurried in hot ethanol (5 mL). The ethanol slurry was cooled to ambient temperature and was further cooled at 5° C. for 0.5 h. The solids were filtered, washed with cold 2-propanol and vacuum dried at 40° C. for 48 h to afford 258.6 mg (79.7%) of an off-white, amorphous powder, mp 174.5–177° C. (d).

Sample No. 3 exhibits a Ki of 542 nM. The low binding constant indicates that the compound exhibits good high affinity binding to certain CNS nicotinic receptors.

Example 4

Sample No. 4 is (4E)-N-Methyl-5-(3-(5-aminopyridin)yl)-4-penten-2-amine Hemigalactarate, which was prepared in accordance with the following techniques:

(4E)-5-(3-(5-Bromopyridin)yl)-4-penten-2-ol

A mixture of 3,5-dibromopyridine (6.00 g, 25.42 mmol), 4-penten-2-ol (2.62 g, 30.50 mmol ), palladium(II) acetate (57 mg, 0.25 mmol), tri-o-tolylphosphine (309 mg, 1.01 mmol), triethylamine (16 mL, 114.40 mmol), and acetonitrile (20 mL) was heated in a sealed glass tube at 140° C. for 14 h. The reaction mixture was cooled to ambient temperature, diluted with water (50 mL) and extracted with chloroform (3×100 mL). The combined extracts were dried over sodium sulfate, filtered and concentrated on a rotary evaporator. The crude product was purified by column chromatography on neutral alumina eluting with ethyl acetate-hexane (2:3) as eluent to yield 4.20 g (68.2%) of a pale-yellow liquid.

(4E)-5-(3-(5-Bromopyridin)yl-4-penten-2-ol p-Toluenesulfonate

To a stirred solution of (4E)-5-(3-(5-bromopyridin)yl)-4-penten-2-ol (1.80 g, 7.40 mmol) in dry dichloromethane (15 mL) and pyridine (5 mL) at 0° C. was added p-toluenesulfonyl chloride (2.82 g, 14.81 mmol). The reaction mixture was stirred for 24 h at ambient temperature. The solvent was removed under vacuum, toluene (10 mL) was added and removed on a rotary evaporator. The crude product was stirred with saturated solution of sodium bicarbonate (100 mL) for 30 min and then extracted with chloroform (4×50 mL). The combined extracts were dried over sodium sulfate and filtered. The solvent was removed on a rotary evaporator to give 2.52 g (86.0%) of a pale-yellow oil.

(4E)-N-Methyl-5-(3-(5-bromopyridin)yl)-4-penten-2-amine

A mixture of (4E)-5-(3-(5-bromopyridin)yl-4-penten-2-ol p-toluenesulfonate (2.52 g, 6.36 mmol) and methylamine (30 mL, 40% solution in water) and methanol (10 mL) was stirred at ambient temperature for 18 h. The reaction mixture was concentrated on rotary evaporator to 25 mL and extracted with chloroform (4×50 mL). The combined extracts were concentrated on a rotary evaporator. The crude product was treated with aqueous hydrochloric acid (10%, 30 mL) at 0–5° C. and stirred for 30 min. The solution was extracted with chloroform (50 mL). The aqueous layer was cooled (0–5° C.), basified with aqueous sodium hydroxide solution to pH 8–9 and extracted with chloroform (4×50 mL). The combined extracts were dried over sodium sulfate, filtered and concentrated a rotary evaporator to yield a pale-yellow oil (0.94 g, 58.1%).

(4E)-N-Methyl-5-(3-(5-aminopyridin)yl)-4-penten-2-amine

A mixture of (4E)-N-methyl-5-(3-(5-bromopyridin)yl)-4-penten-2-amine (70 mg, 0.27 mmol), copper(I) bromide (43 mg, 0.30 mmol) and concentrated aqueous ammonia (30 mL) were heated in a sealed glass tube at 150–160° C. for 18 h. The reaction mixture was cooled to ambient temperature and extracted with chloroform (4×40 mL). The combined extracts were dried over sodium sulfate, filtered and concentrated on a rotary evaporator to furnish 47 mg (89.5%) of a pale-yellow oil.

(4E)-N-Methyl-5-(3-(5-aminopyridin)yl)-4-penten-2-amine Hemigalactarate

To a hot solution of (4E)-N-methyl-5-(3-(5-aminopyridin)yl)-4-penten-2-amine (40 mg, 0.20 mmol) in ethanol (10 mL) was added galactaric acid (21 mg, 0.10 mmol). The mixture was heated to reflux and water (6 drops) was added drop-wise. The solution was filtered to remove some insoluble particles. The filtrate was concentrated to 5 mL and cooled to ambient temperature for 4 h. The precipitate was filtered, washed with anhydrous ether and dried in a vacuum oven at 45° C. for 16 h. The yield was 32 mg (52.5%) of a very light-yellow powder, mp 175–177° C.

Sample No. 4 exhibits a Ki of 1137 nM. The binding constant indicates that the compound exhibits binding to certain CNS nicotinic receptors.

Example 5

Sample No. 5 is (2S)-(4E)-N-methyl-5-[3-(5-isopropoxy-1-oxopyridin)yl)]-4-penten-2-amine, which was prepared in accordance with the following techniques:

5-Bromo-3-isopropoxypyridine

Potassium metal (6.59 g, 168.84 mmol) was dissolved in dry 2-propanol (60.0 mL) under nitrogen. The resulting potassium isopropoxide was heated with 3,5-dibromopyridine (20.00 g, 84.42 mmol) and copper powder (1 g, 5% by weight of 3,5-dibromopyridine) at 140° C. in a sealed glass tube for 14 h. The reaction mixture was cooled to ambient temperature and extracted with diethyl ether (4×200 mL). The combined ether extracts were dried over sodium sulfate, filtered, and concentrated by rotary evaporation. The resulting crude product was purified by column chromatography over aluminum-oxide, eluting with ethyl acetate-hexane (1:9, v/v). Selected fractions were combined and concentrated by rotary evaporation, producing a pale-yellow oil (12.99 g, 71.2%)

(2R)-4-Penten-2-ol (2R)-4-Penten-2-ol was prepared in 82.5% yield from (R)-(+)-propylene oxide according to procedures set forth in A. Kalivretenos, J. K. Stille, and L. S. Hegedus, *J. Org. Chem.* 56: 2883 (1991).

(2R)-(4E)-5-13-(5-isopropoxypyridin)yl)]-4-penten-2-ol

A mixture of 5-bromo-3-isopropoxypyridine (10.26 g, 47.50 mmol), (2R)-4-penten-2-ol (4.91 g, 57.00 mmol), palladium(II) acetate (106 mg, 0.47 mmol), tri-o- tolylphosphine (578 mg, 1.90 mmol), triethylamine (28.46 mL, 204.25 mmol), and acetonitrile (30 mL) were heated in a sealed glass tube at 140° C. for 14 h. The reaction mixture was cooled to ambient temperature, diluted with water, and extracted with chloroform (3×200 mL). The combined chloroform extracts were dried over sodium sulfate, filtered, and concentrated by rotary evaporation to give a pale-yellow oil (8.92 g, 85.0%).

(2R)-(4E)-5-[3-(5-isopropoxypyridin)yl)]-4-penten-2-ol p-Toluenesulfonate

To a stirred solution of (2R)-(4E)-5-[3-(5-isopropoxypyridin)yl)]-4-penten-2-ol (8.50 g, 38.46 mmol) in dry pyridine (30 mL) at 0° C. was added p-toluenesulfonyl chloride (14.67 g, 76.92 mmol). The reaction mixture was stirred for 24 h at ambient temperature. The pyridine was removed by rotary evaporation. Toluene (50 mL) was added to the residue and removed by rotary evaporation. The crude product was stirred with a saturated solution of sodium bicarbonate (100 mL) and extracted with chloroform (3×100 mL). The combined chloroform extracts were dried over sodium sulfate, filtered, and concentrated by rotary evaporation to yield a dark-brown, viscous oil (11.75 g, 81.5%).

(2S)-(4E)-N-Methyl-5-[3-(5-isopropoxypyridin)yl)]-4-penten-2-amine

A mixture of (2R)-(4E)-5-[3-(5-isopropoxypyridin)yl)]-4-penten-2-ol p-toluenesulfonate (11.00 g, 29.33 mmol), methylamine (200 mL, 40% solution in water), and ethyl alcohol (10 mL) was stirred at ambient temperature for 18 h. The resulting solution was extracted with chloroform (3×100 mL). The combined chloroform extracts were dried over sodium sulfate, filtered, and concentrated by rotary evaporation. The crude product was purified by column chromatography over aluminum oxide, eluting with ethyl acetate-methanol (7:3, v/v). Selected fractions were combined and concentrated by rotary evaporation, producing an oil. Further purification by vacuum distillation furnished 2.10 g (31.0%) of a colorless oil, bp 90–100° C. at 0.5 mm Hg.

(2S)-(4E)-N-Methyl-5-[3-(5-isopropoxypyridin)yl)]-4-penten-2-amine Hemigalactarate (2S)-(4E)-N-Methyl-5-[3-(5-isopropoxypyridin)yl)]-4-penten-2-amine (2.00 g, 8.55 mmol) was dissolved in ethyl alcohol (20 mL), assisted by warming to 70° C. The warm solution was treated with galactaric acid (900 mg, 4.27 mmol) in one portion, followed by the drop-wise addition of water (0.5 mL). The solution was filtered while hot to remove some insoluble material. The filtrate was allowed to cool to ambient temperature. The resulting crystals were filtered, washed with anhydrous diethyl ether, and dried under vacuum at 40° C. to yield a white powder (750 mg, 26.0%), mp 140–143° C.

(2S)-(4E)-N-Methyl-N-(tert-butoxycarbonyl)-5-[3-(5-isopropoxypyridin)yl]-4-penten-2-amine (2S)-(4L)-N-Methyl-5-[3-(5-isopropoxypyridin)yl]-4-penten-2-amine hemigalactarate (225.0 mg, 0.663 mmol) was basified with saturated $K_2CO_3$ solution (5 mL), treated with saturated NaCl solution (2 mL), and further basified with 50% NaOH solution (10 drops). The turbid mixture was extracted with $CHCl_3$ (10×7 mL). The combined, light-yellow, $CHCl_3$ extracts were dried ($Na_2SO_4$), filtered, concentrated by rotary evaporation. and dried under high vacuum (1 mm Hg) for 1.5 h to give (150.7 mg) (97.0%) of (2S)-(4E)-N-methyl-5-[3-(5-isopropoxypyridin)yl]-4-penten-2-amine as a yellow oil. The oil was immediately dissolved in dry THF (8 mL, freshly distilled from sodium and benzophenone), and the resulting solution was treated at 0° C. with di-tert-butyl dicarbonate (159.0 mg, 0.729 mmol) under a nitrogen atmosphere. The resulting mixture was stirred and allowed to warm to ambient temperature over 22 h. The solution was concentrated by rotary evaporation and dried under high vacuum (1 mm Hg) producing a yellow oil (232.5 mg). The crude product was purified by column chromatography on silica gel (20 g, Merck 70–230 mesh) eluting with $CHCl_3$—$CH_3OH$ (95:5, v/v). Selected fractions, containing the product ($R_f$ 0.55) were combined, concentrated by rotary evaporation, and vacuum dried briefly at 1 mm Hg to give 226.5 mg (quantitative yield) of a light-yellow oil.

(2S)-(4E)-N-Methyl-N-(tert-butoxycarbonyl)-5-[3-(5-isopropoxy-1-oxopyridin)yl]-4-penten-2-amine An ice-cold (0° C.) solution of (2S)-(4E)-N-methyl-N-(tert-butoxycarbonyl)-5-[3-(5-isopropoxypyridin)yl]-4-penten-2-amine (218.8 mg, 0.654 mmol) in $CH_2Cl_2$ (5 mL, distilled from $LiAlH_4$) was treated with (3-chloroperoxybenzoic acid) (219.1 mg, 0.724–1.092 mmol) (57.86% purity) in one portion. The solution was stirred for 30 min at 0° C., and stored at 5° C. for 16 h. TLC analysis ($CHCl_3$—$CH_3OH$, 95:5, v/v) indicated reaction completion. The light-yellow solution was treated with 1 M NaOH solution (10 mL) and 10% $NaHSO_3$ solution (2 mL). The $CH_2Cl_2$ phase was separated; the aqueous phase was extracted with $CH_2Cl_2$ (2×10 mL). All $CH_2Cl_2$ extracts were combined, dried ($Na_2SO_4$), filtered, concentrated by rotary evaporation, and vacuum dried briefly at 1 mm Hg to give 221.7 mg of a light-yellow oil. The crude product was purified by column chromatography on silica gel (20.8 g, Merck 70–230 mesh) eluting with EtOAc-$CH_3OH$ (9:1, v/v). Selected fractions, containing the product ($R_f$ 0.34) were combined, concentrated by rotary evaporation, and vacuum dried briefly (1.5 h) at 1.3 mm Hg to give 201.2 mg (89.9%) of a pale yellow oil.

(2S)-(4E)-N-Methyl-5-[3-(5-isopropoxy 1-oxopyridin)yl)]-4-penten-2-amine

Under a nitrogen atmosphere, a cold (0° C.), stirring solution of (2S)-(4E)-N-methyl-N-(tert-butoxycarbonyl)-5-[3)-(5-isopropoxy-1-oxopyridin)yl]-4-penten-2-amine (191.6 mg, 0.547 mmol) in anisole (2.5 mL) was treated drop-wise with trifluoroacetic acid (2.5 mL, 32.5 mmol) over 3 min. The resulting light-yellow solution was allowed to stir for 45 min at 0–5° C. and was then concentrated by rotary evaporation using a 70° C. water bath. The resulting liquid was vacuum dried at 1 mm Hg for 16 h to produce a yellow oil (254.5 mg). The oil was basified at 0–5° C. with 1 M NaOH solution (2 mL), followed by treatment with saturated NaCl solution (2 mL). The mixture was extracted with $CHCl_3$ (14×5 mL). The combined CHCl3 extracts were dried ($Na2SO_4$), filtered, concentrated by rotary evaporation, and vacuum dried to give 134.4 mg (98.2%) of a light-yellow oil.

Sample No. 5 exhibits a Ki of 1400 nM. The binding constant indicates that the compound exhibits binding to certain CNS nicotinic receptors. The sample exhibits a neurotransmitter release $E_{max}$ value of 19%.

Sample No. 5 exhibits an $E_{max}$ of 7% (at a concentration of 100 uM) at muscle-type receptors, indicating that the compound does not induce activation of muscle-type receptors. The sample exhibits an $E_{max}$ of 8% (at a concentration of 100 uM) at ganglionic-type receptors. The compound has the capability to activate human CNS receptors without activating muscle-type and ganglionic-type nicotinic acetylcholine receptors to any significant degree. Thus, there is provided a therapeutic window for utilization in the treatment of CNS disorders. That is, at certain levels the compound shows CNS effects to a significant degree but does not show undesirable muscle and ganglia effects to any significant degree.

Example 6

Sample No. 6 is (3E)-N-methyl-4-(3-(5-isobutoxypyridin)yl)-3-buten-1-amine hemigalactarate, which was prepared in accordance with the following techniques:

3-Bromo-5-isobutoxypyridine

Under nitrogen, sodium metal (0.46 g, 20 mmol) was stirred in dry (distilled from sodium) isobutanol (15 mL) until the sodium had completely dissolved (overnight at 25° C. and 1 h at reflux). When the mixture was cooled, it solidified. To this solid, 3,5-dibromopyridine (3.16 g, 13.3 mmol) and anhydrous DMF (15 mL) were added. The mixture was heated at reflux for 24 h, cooled, poured into water (75 mL), and extracted with ether (3×75 mL). The ether extracts were dried ($Na_2SO_4$) and evaporated, and the residue was vacuum distilled to give 1.45 g (47.4% yield) of colorless oil, bp 102–109° C. at 2.0 mm Hg.

(3E)-N-Methyl-N-(tert-butoxycarbonyl)-4-(3-(5-isobutoxypyridin)yl)-3-buten-1-amine A mixture of 3-bromo-5-isobutoxypyridine (690 mg, 3.00 mmol), N-methyl-N-(tert-butoxycarbonyl)-3-buten-1-amine (574 mg, 3.10 mmol), prepared as previously described, palladium(II) acetate (7 mg, 0.03 mmol), and tri-o-tolylphosphine (37 mg, 0.12 mmol) was diluted with acetonitrile (2 mL) and triethylamine (1 mL) and heated at 75° C. for 30 h. The mixture was cooled, poured into water (10 mL), and extracted with chloroform (2×10 mL). The extracts were dried ($Na_2SO_4$) and evaporated. The residue was column chromatographed on Merck silica gel 60 (70–230 mesh) with 15–40% (v/v) ethyl acetate in hexane, producing 754 mg (75.4% yield) of viscous, light-yellow oil.

(3E)-N-Methyl-4-(3-(5-isobutoxypyridin)yl)-3-buten-1-amine (3E)-N-Methyl-N-(tert-butoxycarbonyl)-4-(3-(5-isobutoxypyridin)yl)-3-buten-1-amine (748 mg, 2.24 mmol) was dissolved in THF (15 mL) and diluted with 6 M aqueous HCl (15 mL). The mixture was stirred at 25° C. for 1.5 h and cooled to 0° C., at which point 5 M aqueous NaOH (20 mL) and saturated aqueous NaCl (20 mL) were added. This mixture was extracted with chloroform (3×35 mL), and the extracts were dried ($Na_2SO_4$) and evaporated. The residue was column chromatographed on Merck silica gel 60 (70–230 mesh) with 10–20% (v/v) methanol, 2% (v/v) $Et_3N$ in benzene to give 203 mg (38.7% yield) of waxy, white solid.

(3E)-N-Methyl-4-(3-(5-isobutoxypyridin)yl)-3-buten-1-amine Hemigalactarate (3E)-N-Methyl-4-(3-(5-isobutoxypyridin)yl)-3-buten-1-amine (195 mg, 0.832 mmol) was dissolved in absolute ethanol (3 mL), and galactaric acid (90 mg, 0.42 mmol) and water (1 mL) were added. The mixture was heated in a hot water bath until it clarified and then filtered through a glass wool plug. The filtrate was diluted with ethanol (6 mL) and cooled slowly to 0° C. Vacuum filtration and vacuum oven drying gave 38 mg of the hemigalactarate as a white powder, mp 146–149° C. (d). Evaporation of the filtrate and recrystallization from methanol (3 mL) gave a second crop (24 mg) of the same purity as the first, bringing the combined yield to 62 mg (22.0%).

Sample No. 6 exhibits a Ki of 20 nM. The low binding constant indicates that the compound exhibits good high affinity binding to certain CNS nicotinic receptors. Sample No. 6 exhibits an $EC_{50}$ of 15,000 nM and an $E_{max}$ value of 25% for dopamine release. The sample exhibits an $EC_{50}$ value of 1,000 nM and an $E_{max}$ value of 15% in the rubidium ion flux assay.

Sample No. 6 exhibits an $E_{max}$ of 6% (at a concentration of 100 uM) at muscle-type receptors. The sample exhibits an $E_{max}$ of 13% (at a concentration of 100 uM) at ganglionic-type receptors.

Example 7

Sample No. 7 is (3E)-N-methyl-4-(3-(1-oxopyridin)yl)-3-buten-1-amine, which was prepared in accordance with the following techniques:

(E)-Metanicotine (E)-Metanicotine was prepared from nicotine according to the procedure described in U.S. Pat. No. 5,663,356 to Ruecroft and Woods.

(3E)-N-Methyl-N-(tert-butoxycarbonyl)-4-(3-pyridinyl)-3-buten-1-amine

Di-tert-butyl dicarbonate (425 mg, 1.95 mmol) was added to a cold (ice bath), stirred solution of (3E)-N-methyl-4-(3-pyridinyl)-3-buten-1-amine ((E)-metanicotine)) (317 mg, 1.95 mmol) in 2 mL of THF. The ice bath was removed and the solution was stirred at 25° C. for 16 h. The volatiles were removed and the residue was column chromatographed on Merck silica gel 60 (70–230 mesh) with 1:1 (v/v) ethyl acetate/hexane to give 413 mg (80.8% yield) of a colorless oil.

(3E)-N-Methyl-N-(tert-butoxycarbonyl)-4-(3-(1-oxopyridin)yl)-3-buten-1-amine

Meta-chloroperoxybenzoic acid (57–86%) (425 mg, 1.40–2.12 mmol) was added to a cold (ice bath), stirred solution of (3E)-N-methyl-N-(tert-butoxycarbonyl)-4-(3-pyridinyl)-3-buten-1-amine (405 mg, 1.54 mmol) in dichloromethane (5 mL). The mixture was kept at 4° C. for 16 h and then shaken with a mixture of 1 M aqueous NaOH (10 mL) and 10% (w/v) aqueous $NaHSO_3$ (2 mL). The organic layer was dried ($Na_2SO_4$) and evaporated, leaving 416 mg (96.7% yield) of a colorless, viscous oil ($R_f$ 0.50 on silica gel with 5% methanol in chloroform).

(3E)-N-Methyl-4-(3-(1-oxopyridin)yl)-3-buten-1-amine

To a stirred solution of (3E)-N-methyl-N-(tert-butoxycarbonyl)-4-(3-(1-oxopyridin)yl)-3-buten-1-amine (126 mg, 0.453 mmol) in anisole (1 mL) at 0° C., was added trifluoroacetic acid (1 mL). The mixture was stirred 30 min at 0° C., and then the volatiles were removed, first by rotary evaporator and then under high vacuum. The residue was mixed with 10% (w/v) aqueous NaOH (2 mL) and saturated aqueous NaCl (2 mL), and the mixture was extracted with chloroform (3×3 mL). The extracts were dried (Na2SO$_4$) and evaporated, leaving 47 mg (59% yield) of an off-white, viscous oil ($R_f$ 0.14 on silica gel with 1:1 methanol/chloroform).

Sample No. 7 exhibits a Ki of 47,220 nM.

Example 8

Sample No. 8 is (4E)-N-methyl-5-(3-(1-oxopyridin)yl)-4-penten-2-amine, which was prepared in accordance with the following techniques:

(4E)-5-(3-Pyridyl)-4-penten-2-ol

A mixture of 3-bromopyridine (7.50 g, 47.46 mmol), 4-penten-2-ol (4.90 g, 56.96 mmol), palladium(II) acetate (106 mg, 0.47 mmol), tri-o-tolylphosphine (575 mg, 1.89 mmol), triethylamine (28.4 mL, 204.11 mmol) and acetonitrile (25 mL) were heated in a sealed glass tube at 140° C. for 14 h. The reaction mixture was cooled to ambient temperature, diluted with water, and extracted with chloroform (3×200 mL). The combined chloroform extracts were dried over sodium sulfate, filtered, and concentrated by rotary evaporation to give a pale-yellow oil (7.50 g, 81.0 %).

(4E)-5-(3-Pyridyl)-4-penten-2-ol p-Toluenesulfonate

To a stirred solution of (4E)-5-(3-pyridyl)-4-penten-2-ol (5.00 g, 30.67 mmol) in dry pyridine (30 mL) at 0° C. was added p-toluenesulfonyl chloride (8.77 g, 46.01 mmol). The reaction mixture was stirred for 24 h at ambient temperature. The pyridine was removed by rotary evaporation. Toluene (50 mL) was added to the residue and subsequently removed by rotary evaporation. The crude product was stirred with a saturated solution of sodium bicarbonate (100 mL) and extracted with chloroform (3×100 mL). The combined chloroform extracts were dried over sodium sulfate, filtered, and concentrated by rotary evaporation. The crude product was purified by column chromatography over aluminum oxide, eluting with ethyl acetate-hexane (3:7, v/v). Selected fractions were combined and concentrated by rotary evaporation to give a viscous, brown oil (5.83 g, 60.1%).

(4E)-N-Methyl-5-(3-pyridyl)-4-penten-2-amine

A mixture of (4E)-5-(3-pyridyl)-4-penten-2-ol p-toluenesulfonate (5.60 g, 17.66 mmol), methylamine (100 mL, 40% solution in water), and ethyl alcohol (10 mL) was stirred at ambient temperature for 18 h. The resulting solution was extracted with chloroform (3×100 mL). The combined chloroform extracts were dried over sodium sulfate, filtered, and concentrated by rotary evaporation. The crude product was purified by column chromatography over aluminum oxide, eluting with ethyl acetate-methanol (7:3, v/v). Selected fractions were combined and concentrated by rotary evaporation, producing an oil. Further purification by vacuum distillation furnished 1.60 g (51.6%) of a colorless oil, bp 110–120° C. at 0.1 mm Hg.

(4E)-N-Methyl-5-(3-pyridyl)-4-penten-2-amine Hemigalactarate (4E)-N-Methyl-5-(3-pyridyl)-4-penten-2-amine (1.60 g, 9.10 mmol) was dissolved in ethyl alcohol (20 mL), assisted by warming to 60° C. The warm solution was treated with galactaric acid (955 mg, 4.54 mmol) in one portion, followed by the drop-wise addition of water (0.5 mL). The solution was filtered while hot to remove some insoluble material. The filtrate was allowed to cool to ambient temperature. The resulting crystals were filtered, washed with anhydrous diethyl ether, and dried under vacuum at 40° C. to yield 1.20 g (47.0%) of a white powder, mp 148–150° C.

(4E)-N-Methyl-N-(tert-butoxycarbonyl)-5-(3-pyridyl)-4-penten-2-amine (4E)-N-Methyl-5-(3-pyridyl)-4-penten-2-amine hemigalactarate (255.0 mg, 0.906 mmol) was basified with saturated K$_2$CO$_3$ solution (5 mL), treated with saturated NaCl solution (2 mL), and further basified with 50% NaOH solution (15 drops). The turbid mixture was extracted with CHCl$_3$ (10×6 mL). The combined CHCl$_3$ extracts were dried (MgSO$_4$), filtered, concentrated by rotary evaporation, and dried under high vacuum (0.8 mm Hg) for 1 h to give (140.6 mg) (88.0%) of (4E)-N-methyl-5-(3-pyridyl)-4-penten-2-amine as a yellow oil. The oil was immediately dissolved in dry THF (7 mL, freshly distilled from sodium and benzophenone), and the resulting solution was treated at 0° C. with di-tert-butyl dicarbonate (191.5 mg, 0.878 mmol) under a nitrogen atmosphere. The resulting mixture was stirred and allowed to warm to ambient temperature over 16 h. The solution was concentrated by rotary evaporation and dried under high vacuum for 1 h producing a yellow oil (226.1 mg). The crude product was purified by column chromatography on silica gel (20 g, Merck 70–230 mesh) eluting with CHCl$_3$—CH$_3$OH (95:5, v/v). Selected fractions, containing the product ($R_f$ 0.48), were combined, concentrated by rotary evaporation, and vacuum dried briefly at 1 mm Hg to give 217.9 mg (98.8%) of a yellow oil.

(4E)-N-Methyl-N-(tert-butoxycarbonyl)-5-(3-(1-oxopyridin)yl)-4-penten-2-amine

An ice-cold (0° C.) solution of (4E)-N-methyl-N-(tert-butoxycarbonyl)-5-(3-pyridyl)-4-penten-2-amine (216.7 mg, 0.7841 mmol) in CH$_2$Cl$_2$ (5 mL) was treated with (3-chloroperoxybenzoic acid) (154.7 mg, 0.511–0.771 mmol) (57–86% purity) in one portion. After stirring for 30 min at 0° C., TLC analysis indicated an incomplete reaction ($R_f$ 0.5 for the Boc-protected amine, $R_f$ 0.08–0.15 for the Boc-protected amine N-oxide), and additional 3-chloroperoxybenzoic acid (64.7 mg, 0.2137–0.3224 mmol) was added. After storage at 5° C. for 16 h, the solution was treated with 1 M NaOH solution (10 mL) and 10% NaHSO$_3$ solution (2 mL). The CH$_2$Cl$_2$ phase was separated; the aqueous phase was extracted with CH$_2$Cl$_2$ (2×5 mL). All CH$_2$Cl$_2$ extracts were combined, dried (Na$_2$SO$_4$), filtered, concentrated by rotary evaporation, and vacuum dried briefly at 1.5 mm Hg to give 221.6 mg (96.7%) of a yellow oil.

(4E)-N-Methyl-5-(3-(1-oxopyridin)yl)-4-penten-2-amine

Under a nitrogen atmosphere, a cold (0° C.), stirring solution of (4E)-N-methyl-N-(tert-butoxycarbonyl)-5-(3-(1-oxopyridin)yl)-4-penten-2-amine (215.9 mg, 0.738 mmol) in anisole (2.5 mL) was treated drop-wise with trifluoroacetic acid (2.5 mL, 32.5 mmol) over 3 min. The resulting light-yellow solution was allowed to stir for 45 min at 0–5° C. and was then concentrated by rotary evaporation using a 70° C. water bath. The resulting liquid was vacuum dried at 0.5 mm Hg for 16 h to produce a light-yellow oil (302.5 mg). The oil was basified at 0–5° C. with 1 M NaOH solution (2 mL), followed by treatment with saturated NaCl solution (2 mL). The mixture was extracted with CHCl$_3$ (14×5 mL). The combined CHCl$_3$ extracts were dried (Na$_2$SO$_4$), filtered, concentrated by rotary evaporation, and vacuum dried to give 143.8 mg (quantitative yield) of a brown, syrupy semi-solid ($R_f$ 0.23 in $CH_3OH-Et_3N$ (97:3, v/v)).

Sample No. 8 exhibits a Ki of 5900 nM. The binding constant indicates that the compound exhibits binding to certain CNS nicotinic receptors. The sample exhibits a neurotransmitter release $E_{max}$ value of 9%.

Sample No. 8 exhibits an $E_{max}$ of 0% (at a concentration of 100 uM) at muscle-type receptors, indicating that the compound does not induce activation of muscle-type receptors. The sample exhibits an $E_{max}$ of 8% (at a concentration of 100 uM) at ganglionic-type receptors. The compound has the capability to activate human CNS receptors without activating muscle-type and ganglionic-type nicotinic acetylcholine receptors to any significant degree. Thus, there is provided a therapeutic window for utilization in the treatment of CNS disorders. That is, at certain levels the compound shows CNS effects to a significant degree but do not show undesirable muscle or ganglion effects to any significant degree.

Example 9

Sample No. 9 is (3 E)-N-methyl-4-(3-(5-ethylthiopyridin) yl)-3-buten-1-amine hemigalactarate, which was prepared in accordance with the following techniques:

3-Bromo-5-ethylthiopyridine

Under a nitrogen atmosphere, NaOH (1.25 g, 31.3 mmol) was added to anhydrous DMF (40 mL). Ethanethiol (2.60 mL, 2.20 g, 35.5 mmol) was then added by syringe and the mixture was stirred for 6 h at 25° C. while the NaOH dissolved. The solution was cooled to 0° C., and 3,5-dibromopyridine (5.92 g, 25.0 mmol) was added. After stirring for 15 min at 0° C. and 45 min at 25° C., the mixture was poured into water (250 mL) and extracted with ether (2×100 mL). Drying ($Na_2SO_4$) and evaporation of the ether, followed by vacuum distillation of the crude product gave 4.39 g (80.6% yield) of colorless oil, bp 91–95° C. at 0.30 mm Hg.

(3E)-N-Methyl-N-(tert-butoxycarbonyl)-4-(3-(5-ethylthiopyridin)yl)-3-buten-1-amine A mixture of 3-bromo-5-ethylthiopyridine (1.09 g, 5.00 mmol), N-methyl-N-(tert-butoxycarbonyl)-3-buten-1-amine (945 mg, 5.10 mmol), prepared as previously described, palladium(II) acetate (11 mg, 0.049 mmol), and tri-o-tolylphosphine (61 mg, 0.20 mmol) was diluted with acetonitrile (3 mL) and triethylamine (1.5 mL) and heated at 75° C. for 40 h. Another 11 mg of palladium(II) acetate and 61 mg of tri-o-tolylphosphine were added and heating was continued for another 32 h. The mixture was cooled, poured into water (15 mL), and extracted with chloroform (2×15 mL). The extracts were dried ($Na_2SO_4$) and evaporated, and the residue was column chromatographed on Merck silica gel 60 (70–230 mesh) using a 15–30% (v/v) gradient of ethyl acetate in hexane. This gave 1.28 g (79.5% yield) of light-yellow, viscous oil ($R_f$ 0.10 in 17% ethyl acetate in hexane).

(3E)-N-Methyl-4[3-(5-ethylthiopyridin)yl]-3-buten-1-amine (3E)-N-Methyl-N-(tert-butoxycarbonyl)-4-(3-(5-ethylthiopyridin)yl)-3-buten-1-amine (1.27 g, 3.94 mmol) was dissolved in THF (25 mL) and cooled to 0° C., at which point 6 M aqueous HCl (25 mL) was added. The mixture was stirred for 75 min at 25° C. and cooled again to ice bath temperature as 5 M aqueous NaOH (35 mL) was added. Saturated aqueous NaCl (35 mL) was then added and the mixture was extracted with chloroform (3×100 mL). Drying ($Na_2SO_4$) and evaporation of the extracts, followed by column chromatography on 30 g of Merck silica gel 60 (70–230 mesh) using 25% (v/v) methanol, 2.5% (v/v) triethylamine in benzene, gave 190 mg of light-yellow oil. Recovered starting material was treated again with aqueous HCl in THF (2.5 h at 25° C.) to give an additional 82 mg of desired product, bringing the total weight to 272 mg (31.1 % yield).

(3E)-N-Methyl-4-(3-(5-ethylthiopyridin)yl)-3-buten-1-amine Hemigalactarate (3E)-N-Methyl-4-(3-(5-ethylthiopyridin)yl)-3-buten-1-amine (265 mg, 1.19 mmol) was dissolved in absolute ethanol (4 mL), and galactaric acid (128 mg, 0.591 mmol) and water (1 mL) were added. The mixture was heated in a hot water bath until it clarified and then filtered through a glass wool plug to remove a small amount of insoluble material. The flask and the filter were washed with 4:1 (v/v) ethanol/water (2 mL) and the wash was added to the filtrate. The filtrate was diluted with ethanol (6 mL) and cooled slowly to 0° C. Vacuum filtration and vacuum oven drying (40° C., 24 h) gave 281 mg (72.8% yield) of white powder, mp 162–164° C. (d).

Sample No. 9 exhibits a Ki of 28 nM. The low binding constant indicates that the compound exhibits good high affinity binding to certain CNS nicotinic receptors. Sample No. 9 exhibits an $EC_{50}$ value of 875 nM and an $E_{max}$ value of 39% for dopamine release, indicating that the compound elicts neurotransmitter release. The sample exhibits an $EC_{50}$ value of 191 nM and an $E_{max}$ value of 40% in the rubidium ion flux assay.

Sample No. 9 exhibits an $E_{max}$ of 7% (at a concentration of 100 uM) at muscle-type receptors. The sample exhibits an $E_{max}$ of 22% (at a concentration of 100 uM) at ganglionic-type receptors.

Example 10

Sample No. 10 is of (4E)-N-methyl-5-(3-(5-trifluoromethylpyridin)yl)-4-penten-2-amine, which was prepared in accordance with the following techniques:

(4E)-5-(3-(5-Trifluoromethylpyridin)yl)-4-penten-2-ol

A mixture of 3-chloro-5-trifluoromethylpyridine (4.00 g, 22.03 mmol) (Strem Chemicals Inc.), 4-penten-2-ol (2.28 g, 26.44 mmol), palladium(II) acetate (50 mg, 0.22 mmol), tri-o-tolylphosphine (270 mg, 0.88 mmol), triethylamine (13.8 mL, 99.15 mmol) and acetonitrile (15 mL) was heated in a sealed glass tube at 140° C. for 14 h. The reaction mixture was cooled to ambient temperature, diluted with water (40 mL) and extracted with chloroform (3×100 mL). The combined extracts were dried over anhydrous sodium sulfate, filtered and concentrated on a rotary evaporator to furnish 2.31 g (45.2%) of a colorless, viscous oil.

(4E)-5-(3-(5-Trifluoromethylpyridinyl)-4-penten-2-ol p-Toluenesulfonate

To a stirred solution of (4E)-5-(3-(5-trifluoromethylpyridin)yl)-4-penten-2-ol (2.10 g, 9.09 mmol) in dry pyridine (15 mL) at 0° C. was added p-toluenesulfonyl chloride (5.20 g, 27.27 mmol). The reaction mixture was stirred for 24 h at ambient temperature. The pyridine was removed under vacuum, toluene (20 mL) was added and removed on a rotary evaporator. The crude product was stirred with saturated solution of sodium bicarbonate (100 mL) for 30 min and then extracted with chloroform (4×75 mL). The combined extracts were dried over sodium sulfate, filtered and concentrated on a rotary evaporator to furnish a dark-brown, viscous oil (2.57 g, 73.5%)

(4E)-5-(3-(5-Trifluoromethylpyridin)yl)-4-penten-2-amine

A mixture of (4E)-5-(3-(5-trifluoromethylpyridinyl)-4-penten-2-ol p-toluenesulfonate (2.30 g, 5.97 mmol) methylamine (50 mL, 40% solution in water) and ethyl alcohol (5 mL) was stirred at ambient temperature for 18 h. The mixture was extracted with chloroform (3×100 mL). The combined chloroform extracts were dried over sodium sulfate, filtered and concentrated on a rotary evaporator. The crude product was purified by column chromatography on neutral alumina, eluting with ethyl acetate-methanol (3:7) to yield a dark-brown solid. The product was further purified by recrystallization from chloroform-hexane to yield 650 mg (44.4%) of a pale-yellow crystalline solid, mp 144–147° C.

Sample No. 10 exhibits a Ki of 3942 nM. The binding constant indicates that the compound exhibits binding to certain CNS nicotinic receptors. The sample exhibits an $EC_{50}$ value of 100,000 nM and an $E_{max}$ value of 0% in the rubidium ion flux assay. The sample exhibits a neurotransmitter release $E_{max}$ value of 50%.

Sample No. 10 exhibits an $E_{max}$ of 0% (at a concentration of 100 uM) at muscle-type receptors. The sample exhibits an $E_{max}$ of 0% (at a concentration of 100 uM) at ganglionic-type receptors.

Example 11

Sample No. 11 is (4E)-N-methyl-5-(3-(5-((carboxymethyl)oxy)pyridin)yl)-4-penten-2-amine, which was prepared in accordance with the following techniques:

A solution of (4E)-N-methyl-N-(tert-butoxycarbonyl)-5-(3-(5-hydroxypyridin)yl)-4-penten-2-amine (156 mg, 0.534 mmol), prepared as previously described, in absolute ethanol (5 mL) was cooled to 0° C. and sequentially treated, drop-wise, with 5.0 M aqueous NaOH (0.11 mL, 0.55 mmol) and a solution of iodoacetic acid (149 mg, 0.801 mmol) in 5.0 M aqueous NaOH (0.15 mL, 0.75 mmol). A precipitate formed. The mixture was warmed to 25° C. and enough water (~0.5 mL) was added to dissolve the precipitate. The homogeneous solution was stirred for 24 h and then treated with another drop of 5.0 M NaOH. After stirring for another 24 h, the mixture was concentrated to dryness. The residue was dissolved in 6.0 M HCl (4 ml, 24 mmol) and stirred for 1 h at 25° C. The volatiles were again evaporated, and the residue was dissolved in 1% (v/v) aqueous acetic acid and applied to a Dowex 50 column. Washing successively with water and 1% (v/v) aqueous ammonia gave, after lyophilization, 93 mg of an off-white powder. Recrystallization from isopropanol gave 17 mg of a white powder, mp 160–165° C. (d).

Sample No. 111 is determined to exhibit a Ki of 100,000 nM.

Example 12

Sample No. 12 is (4E)-5-(3-(5-isopropoxypyridin)yl)-4-penten-2-amine hemigalactarate, which was prepared in accordance with the following techniques:

N-(4-(1-Penten)yl)phthalimide

To a stirred solution of 4-penten-2-ol (5.00 g, 58.1 mmol), phthalimide (8.55 g, 58.1 mmol), and triphenylphosphine (15.2 g, 58.1 mmol) in THF (40 mL), at 0° C. under nitrogen, was added a solution of diethyl azodicarboxylate (10.1 g, 58.1 mmol) in THF (20 mL) dropwise. The mixture was stirred at 0° C. (12 h) and then at 25° C. (12 h). The mixture was diluted with water and extracted three times with chloroform. The chloroform extracts were dried ($Na_2SO_4$), evaporated and column chromatographed on Merck silica gel 60 (70–230 mesh) with chloroform to give 8.77 g (70.2% yield) of colorless oil.

(4E)-N-Phthaloyl-5-(3-(5-isoproxypyridin)yl)-4-penten-2-amine

A mixture of palladium(II) acetate (2.2 mg, 0.010 mmol), tri-o-tolylphosphine (12 mg, 0.040 mmol), 3-bromo-5-isopropoxypyridine (216 mg, 1.00 mmol), and N-(4-(1-penten)yl)phthalimide (215 mg, 1.00 mmol) was diluted with acetonitrile (1.0 mL) and triethylamine (0.5 mL) and heated (80° C. oil bath) under nitrogen for 25 h. The mixture was cooled, poured into water (5 mL) and extracted with chloroform (3×5 mL). The extracts were dried ($Na_2SO_4$), evaporated and column chromatographed on 15 g of Merck silica gel 60 (70–230 mesh) with 1:1:3 (v/v) ethyl acetate/chloroform/hexane to give 268 mg (76.6% yield) of very viscous, light yellow oil.

(4E)-5-(3-(5-Isopropoxypyridin)yl)-4-penten-2-amine (4E)-N-Phthaloyl-5-(3-(5-isoproxypyridin)yl)-4-penten-2-amine (258 mg, 0.736 mmol) was dissolved in methanol (4 mL) and treated with hydrazine hydrate (0.15 mL, 3.1 mmol) and stirred under nitrogen at 25° C. for 36 h. The reaction mixture was then poured into a mixture of 1 M NaOH solution (15 mL) and saturated NaCl solution (15 mL) and extracted with benzene (3×15 mL). The benzene extracts were dried ($Na_2SO_4$), evaporated and column chromatographed on 7 g of Merck silica gel 60 (70–230 mesh) with 5–10% (v/v) methanol, 2.5% (v/v) triethylamine in benzene. This provided 118 mg (72.8% yield) of light yellow oil.

(4E)-5-(3-(5-Isopropoxypyridin)yl)-4-penten-2-amine Hemigalactarate (4E)-5-(3-(5-Isopropoxypyridin)yl)-4-penten-2-amine (112 mg, 0.508 mmol) was dissolved in methanol (2.5 mL) and treated with galactaric acid (53 mg, 0.25 mmol) and water (0.20 mL). The mixture was warmed slightly, filtered through a glass wool plug and cooled slowly to 0° C., at which temperature it remained for 48 h. Vacuum filtration and vacuum oven drying (40° C., 24 h) gave 53 mg of white solid (mp l71.5–173.5° C.). Second and third crops of 50 mg and 5 mg (mp 170–173° C. and 169–172° C. respectively) were isolated by concentrating the supernatant, bringing the total yield to 108 mg (65.5% yield). The three salt samples were slurried together in hot 100% ethanol, cooled, and filtered to give an analytical sample of 27 mg of fine, white powder, mp 170–172° C.

Sample No. 12 exhibits a Ki of 413 nM. The binding constant indicates that the compound exhibits binding to certain CNS nicotinic receptors.

Sample No. 12 exhibits an $E_{max}$ of 13% (at a concentration of 100 uM) at muscle-type receptors. The sample exhibits an $E_{max}$ of 5% (at a concentration of 100 uM) at ganglionic-type receptors. The sample exhibits a neurotransmitter $E_{max}$ of 32%.

Example 13

Sample No. 13 is of (4E)-N-methyl-5-(3-(5-hydroxypyridin)yl)-4-penten-2-amine sesquioxalate, which was prepared in accordance with the following techniques:

3-Bromo-5-hydroxypyridine

3-Bromo-5-hydroxypyridine was prepared in 35.0% yield from furfurylamine according to the procedure described in U.S. Pat. No. 4,192,946 to Clauson-Kaas et al.

(4E)-N-Methyl-N-(tert-butoxycarbonyl)-5-(3-(5-hydroxypyridin)yl)-4-penten-2-amine A mixture of palladium(II) acetate (65 mg, 0.28 mmol), tri-o-tolylphosphine (354 mg, 1.11 mmol), 3-bromo-5-hydroxypyridine (3.20 g, 18.4 mmol), and N-methyl-N-(tert-butoxycarbonyl)-4-penten-2-amine (3.66 g, 18.4 mmol), prepared as previously described, was diluted with triethylamine (8 mL) and acetonitrile (11 mL). The mixture was heated and stirred under nitrogen in a sealed tube at 120° C. for 24 h. The mixture was cooled, poured into water and extracted with chloroform. The extracts were dried ($Na_2SO_4$), evaporated and column chromatographed on Merck silica gel 60 (70–230 mesh) with 20–30% (v/v) acetone in chloroform. This gave 3.6 g (67% yield) of pale yellow oil.

(4E)-N-Methyl-5-(3-(5-hydroxypyridin)yl)-4-penten-2-amine

Gaseous HCl was bubbled into a stirred solution of (4E)-N-methyl-N-(tert-butoxycarbonyl)-5-(3-(5-hydroxypyridin)yl)-4-penten-2-amine (341 mg, 1.17 mmol) in anisole (1 mL) at 25° C. A brief induction period was followed by rapid gas evolution and the formation of a gummy solid. The HCl stream was turned off and the volatiles were evaporated, first in a stream of nitrogen gas and then under high vacuum. The residue was dissolved in methanol and filtered. The filtrate was rotary evaporated, leaving 316 mg of dark, semisolid material that still smelled of anisole. This material was combined with another preparation containing ~120 mg of the impure amine and chromatographed on 15 g of Merck silica gel 60 (70–230 mesh) with 5:35:60 (v/v) triethylamine/methanol/chloroform. This gave 201 mg of brown gum.

(4E)-N-Methyl-5-(3-(5-hydroxypyridin)yl)-4-penten-2-amine Sesquioxalate

To a solution of (4E)-N-methyl-5-(3-(5-hydroxypyridin)yl)-4-penten-2-amine (83 mg, 0.43 mmol) in methanol (7 mL) was added 38 mg (0.43 mmol) of oxalic acid. The oxalic acid dissolved. The mixture was kept at 25° C for 6 h and the supernatant was drawn off. The precipitate was dried in the vacuum oven (40° C.) overnight to give 59 mg (49% yield) of fine, light yellow crystals (mp 161–163° C.).

Sample No. 13 exhibits a Ki of 504 nM. The binding constant indicates that the compound exhibits binding to certain CNS nicotinic receptors. The sample exhibits a neurotransmitter release $E_{max}$ value of 80%.

Sample No. 13 exhibits an $E_{max}$ of 21 % (at a concentration of 100 uM) at muscle-type receptors. The sample exhibits an $E_{max}$ of 12% (at a concentration of 100 uM) at ganglionic-type receptors.

The foregoing is illustrative of the present invention and is not to be construed as limiting thereof. The invention is defined by the following claims, with equivalents of the claims to be included therein.

That which is claimed is:

1. A compound of the formula:

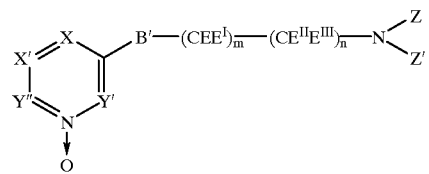

where X, X', Y' and Y" are individually carbon bonded to a substituent species characterized as having a sigma m value between about −0.3 to about 0.75; m and n are integers such that the sum of m plus n is 1, 2, 3, 4, 5 or 6; B' is a two carbon bridging species; Z and Z' are individually hydrogen or methyl; and E, $E^I$, $E^{II}$ and $E^{III}$ are individually hydrogen or methyl.

2. The compound of claim 1, wherein B' is CR'=CR', wherein each R' is individually hydrogen or methyl.

3. The compound of claim 1, wherein Y' and Y" each are carbon bonded to hydrogen.

4. The compound of claim 1, wherein m is 1 and n is 1.

5. The compound of claim 1, wherein X' is CH, CBr or COR', wherein R' is hydrogen or alkyl.

6. A pharmaceutical composition comprising an amount of a compound of the formula:

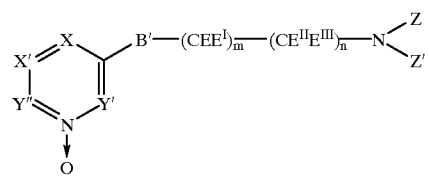

in association with a pharmaceutically acceptable carrier, where X, X', Y' and Y" are individually carbon bonded to a substituent species characterized as having a sigma m value between about −0.3 to about 0.75; m and n are integers such that the sum of m plus n is 1, 2, 3, 4, 5 or 6; B' is a two carbon bridging species; Z and Z' are individually hydrogen or methyl; and E, $E^I$, $E^{II}$ and $E^{III}$ are individually hydrogen or methyl.

7. The pharmaceutical composition of claim 6, wherein B' is CR'=CR', wherein each R' is individually hydrogen or methyl.

8. The pharmaceutical composition of claim 6, wherein Y' and Y" each are carbon bonded to hydrogen.

9. The pharmaceutical composition of claim 6, wherein m is 1 and n is 1.

10. The pharmaceutical composition of claim 6, wherein X' is CH, CBr or COR', wherein R' is hydrogen or alkyl.

11. A method for treating a disorder characterized by alteration in normal neurotransmitter release comprising administering to a subject in need thereof an effective amount of a compound of the formula:

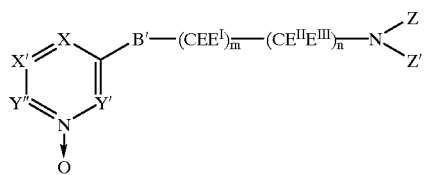

where X, X', Y' and Y" are individually carbon bonded to a substituent species characterized as having a sigma m value between about −0.3 to about 0.75; m and n are integers such that the sum of m plus n is 1, 2, 3, 4, 5 or 6; B' is a two carbon bridging species; Z and Z' are individually hydrogen or methyl; and E, E$^I$, E$^{II}$ and E$^{III}$ are individually hydrogen or methyl.

12. The method of claim 11, whereby B' is CR'=CR', wherein each R' is individually hydrogen or methyl.

13. The method of claim 11, whereby Y' and Y" each are carbon bonded to hydrogen.

14. The method of claim 11, whereby m is 1 and n is 1.

15. The method of claim 11, whereby X' is CH, CBr or COR', wherein R' is hydrogen or alkyl.

* * * * *